United States Patent
Lewis et al.

(10) Patent No.: US 6,890,715 B1
(45) Date of Patent: May 10, 2005

(54) SENSORS OF CONDUCTING AND INSULATING COMPOSITES

(75) Inventors: Nathan S. Lewis, La Canada, CA (US); Robert H. Grubbs, South Pasadena, CA (US); Gregory Sotzing, Willington, CT (US)

(73) Assignee: The California Institute of Technology, Pasadena, CA (US)

( * ) Notice: Subject to any disclaimer, the term of this patent is extended or adjusted under 35 U.S.C. 154(b) by 32 days.

(21) Appl. No.: 09/642,115

(22) Filed: Aug. 18, 2000

Related U.S. Application Data

(60) Provisional application No. 60/149,885, filed on Aug. 18, 1999.

(51) Int. Cl.[7] .............................. C12Q 1/68; C13M 1/00; G01N 27/26
(52) U.S. Cl. ..................... 435/6; 435/283.1; 435/287.2; 435/287.8; 435/287.9; 204/405; 204/416; 204/418; 204/419; 549/4; 549/10; 549/11; 549/12; 549/59; 549/62; 528/380
(58) Field of Search .......................... 702/19; 435/287.9, 435/283.1, 817, 287.7, 287.8; 204/403, 418, 415, 416, 414, 287.7, 287.8; 549/59, 62, 4, 10, 11, 12; 528/380

(56) References Cited

U.S. PATENT DOCUMENTS

| | | | |
|---|---|---|---|
| 4,225,410 A | 9/1980 | Pace | |
| 4,772,559 A | 9/1988 | Preti et al. | |
| 4,911,801 A | 3/1990 | Pons | |
| 5,215,820 A | 6/1993 | Hosokawa et al. | |
| 5,225,110 A | 7/1993 | Kathirgamanathan | |
| 5,352,574 A | 10/1994 | Guiseppi-Elie | |
| 5,407,699 A | 4/1995 | Myers | |
| 5,415,893 A | 5/1995 | Wiersma et al. | |
| 5,498,372 A | 3/1996 | Hedges | |
| 5,519,147 A | * 5/1996 | Swager et al. | |
| 5,536,473 A | 7/1996 | Monkman et al. | |
| 5,674,752 A | 10/1997 | Buckley et al. | |
| 5,756,879 A | 5/1998 | Yamagishi et al. | |
| 5,766,934 A | * 6/1998 | Guiseppi-Elie | |
| 5,801,297 A | 9/1998 | Mifsud et al. | |
| 5,807,701 A | 9/1998 | Payne et al. | |
| 6,315,956 B1 | 11/2001 | Foulger | |
| 6,441,395 B1 | * 8/2002 | Yu et al. ......................... | 257/40 |
| 2002/0141901 A1 | * 10/2002 | Lewis et al. ............... | 422/82.01 |

FOREIGN PATENT DOCUMENTS

| | | |
|---|---|---|
| EP | 0 878 711 | 11/1998 |
| WO | WO 9090027 | 8/1990 |
| WO | WO 9607901 | 3/1996 |
| WO | WO 99/00663 | 1/1999 |
| WO | WO 99/08105 | 2/1999 |
| WO | WO 99/40423 | 8/1999 |
| WO | WO 99/47905 | 9/1999 |
| WO | WO 99/53287 | 10/1999 |

(Continued)

OTHER PUBLICATIONS

Lefebvre, M. et al., Chemical Synthesis, Characterization, and Electrochemical Studies of Poly . . . , Chem. Mater 1999, vol. 11, pp. 262–268.*

(Continued)

*Primary Examiner*—BJ Forman
(74) *Attorney, Agent, or Firm*—Burns Doane Swecker & Mathis, LLP

(57) ABSTRACT

The present invention provides a class of sensors prepared from at least a first material having a positive temperature coefficient of resistance and a second non-conductive or insulating material compositionally different than the first material that show an increase sensitivity detection limit for polar and non-polar analytes. The sensors have applications in the detection of analytes in the environment, associated with diseases and microorganisms.

11 Claims, 17 Drawing Sheets

FOREIGN PATENT DOCUMENTS

| | | |
|---|---|---|
| WO | WO 99/53300 | 10/1999 |
| WO | WO 99/61902 | 12/1999 |
| WO | WO 99/66304 | 12/1999 |
| WO | WO 99/67627 | 12/1999 |
| WO | WO 00/00808 | 1/2000 |
| WO | WO 00/26638 | 5/2000 |
| WO | WO 00/33062 | 6/2000 |

OTHER PUBLICATIONS

Baldacci et al., "Discrimination of Wine Using Taste and Smell Sensors," Sensors and Materials, vol. 10, No. 3 (1998) pp. 185–200.

Breheret et al., "On–line differentiation of mushrooms aromas by combined Headspace/multi–odour gas sensors devices," Bioflavour 95, Dijon (France), Feb. 14–17, 1995, pp. 103–107.

Bruschi et al., "Gas sensing with conducting polymer thin film resistors obtained from commercial photoresist patterns," Proceedings of the $1^{st}$ Italian Conference, 64 BUAX, 1996, pp. 69–73.

Butterworth, et al., "Zeta Potential Measurements on Conducting Polymer–Inorganic Oxide Nanocomposite Particles," Journal of Colloid and Interface Science, 174, pp. 510–517, 1995.

Casella et al., "Copper dispersed into polyaniline films as an amperometric sensor in alkaline solutions of amino acids and polyhydric compounds," Analytica Chimica Acta 335 (1996) pp. 217–225.

Forsyth et al., "Dielectric properties of conductive composites at microwave frequencies," New Horizons for Materials, P. Vincenzini (Ed.), © Techna Srl, pp. 279–286, 1995.

Laranjeira et al., "A conductimetric system based on polyaniline for determination of ammonia in fertilizers," Analytical Letters, 30(12), pp. 2189–2209, 1997.

Luinge et al., "Trace–level identity confirmation from infrared spectra by library searching and artificial neural networks," Analytica Chimica Acta 345 (1997) pp. 173–184.

Meister et al., "Polymer–oxide–silicon–field–effect–transistor (POSFET) as sensor for gases and vapors," Electrochemical Society Proceedings vol. 97–19, pp. 16–22.

Moy et al., "Transient signal modeling for fast odour classification," Bioflavour 95, Dijon (France), Feb. 14–17, pp. 55–58, 1995.

Neaves et al., "A new generation of integrated electronic noses," Sensors and Actuators B 26–27 (1995) pp. 223–231.

Partch et al., "Conducting Polymer Composites, Polypyrrole—Metal Oxide Latexes," © 1992 American Chemical Society, pp. 368–386.

Paulsson et al., "Breath alcohol, multi sensor arrays and electronic noses," SPIE vol. 2932, pp. 84–90, 1997.

Rajeshwar et al., "Polypyrrole composites containing platinum or carbon black: from synthesis to novel applications," Polymer Preprints, vol. 35, No. 1, Am. Chem. Soc., 1994.

Thackery et al., "Chemically Responsive Microelectrochemical Devices Based on Platinized Poly(3–methylthlophene): Variation in Conductivity with Variation in Hydrogen, Oxygen, or pH in Aqueous Solution," J. Phys. Chem., 90, pp. 6674–6679, 1986.

Tourillon et al., "Dispersive X–ray Spectroscopy for Time–Resolved In Situ Observation of Electrochemical Inclusion of Metallic Clusters within a Conducting Polymer," Physical Review Letters, vol. 57, No. 5, pp. 603–606, 1986.

Udrea et al., "Design of a silicon microsensor array device for gas analysis," Microelectronics Journal 27, pp. 449–457, 1996.

Wampler et al., "Composites of Polypyrrole and Carbon Black. 2. Electrosynthesis, Characterization, and Influence of Carbon Black Characteristics," Chem. Mater, 7, pp. 585–592, 1995.

Yamato et al., "A new method for dispersing palladium microparticles in conducting polymer films and its application to biosensors," Synthetic Metals 87, pp. 231–236, 1997.

deLacy Costello et al., "Novel composite organic–inorganic semiconductor sensors for the quantitative detection of target organic vapours," J. Mater. Chem. 6(3):289–294 (1996).

Dickinson et al., "Generating Sensor Diversity through Combinatorial Polymer Synthesis," Anal. Chem. 69:3413–3418 (1997).

Doleman et al., "Quantitative Study of the Resolving Power of Arrays of Carbon Black–Polymer Composites in Various Vapor–Sensing Tasks," Anal. Chem. 70:4177–4190 (1998).

Domansky et al., "Development and Calibration of Field–Effect Transistor–Based Sensor Array for Measurement of Hydrogen and Ammonia Gas Mixtures in Humid Air," Anal. Chem. 70:473–481 (1998).

Freund and Lewis, "A chemically diverse conducting polymer–based 'electronic nose'," Proc. Natl. Acad. Sci. USA 92:2652–2656 (1995).

J. Lipman, "E–noses nose out traditional odor–detection equipment," EDN Magazine (Dec. 17, 1998).

Lonergan et al., "Array–Based Vapor Sensing Using Chemically Sensitive, Carbon Black–Polymer Resistors," Chem. Mater. 8:2298–2312 (1996).

Pearc et al., "Electronic Nose for Monitoring the Flavour of Beers," Analyst 118:371–377 (1993).

Slater et al., "Multi–layer Conducting Polymer Gas Sensor Arrays for Olfactory Sensing," Analyst 118:379–384 (1993).

Chandiok S., "Screening for Bacterial Vaginosis: a Novel Application of Artificial Nose Technology", J. Clin. Pathol., 1997, vol. 50, pp. 790–795.

Preti G., "Analysis of Lung Air from Patients with Bronchogenic Carcinoma and Controls Using Gas Chromatography–Mass Spectrometry," Journal of Chromatography Biomedical Applications, 1988, vol. 432, pp. 1–11.

Simenhoff, M.L., "Biochemical Profile of Lung Breath," The New England Journal of Medicine, Jul. 21, 1977, pp. 132–135.

Vecinana–Nogues, M.T., "Biogenic Amines as Hygenic Quality Indicators of Tuna," J. Agric. Food. Chem., 1997, vol. 45, pp. 2036–2041.

\* cited by examiner

Average % ΔR$_{max}$/R$_b$ values for PEDOT-PSS detectors upon exposure to 16 different analytes at 5% of their vapor pressure

| Detector | Hexane | Benzene | Toluene | Methoxybenzene | Chloroform | Chlorobenzene | Ethyl Acetate | THF |
|---|---|---|---|---|---|---|---|---|
| 1 | -0.012 (6) | 0.07 (4) | 0.05 (7) | 0.20 (8) | 0.12 (9) | 0.2 (1) | 0.1 (1) | -0.012 (6) |
| 2 | -0.03 (1) | 0.14 (8) | 0.07 (8) | 0.3 (1) | 0.2 (1) | 0.4 (2) | 0.2 (2) | -0.02 (1) |
| 3 | -0.03 (1) | 0.1 (1) | 0.04 (3) | 0.3 (1) | 0.07 (4) | 0.4 (2) | 0.14 (6) | -0.02 (1) |
| 4 | -0.012 (7) | 0.1 (1) | 0.06 (7) | 0.3 (1) | 0.2 (1) | 0.3 (2) | 0.2 (2) | -0.012 (6) |
| 5 | -0.010 (5) | 0.1 (1) | 0.05 (6) | 0.2 (1) | 0.17 (9) | 0.3 (1) | 0.2 (2) | -0.011 (6) |
| 6 | -0.006 (4) | 0.06 (8) | 0.05 (7) | 0.16 (7) | 0.10 (9) | 0.2 (1) | 0.1 (1) | -0.004 (2) |
| 7 | -0.010 (7) | 0.1 (2) | 0.07 (8) | 0.3 (2) | 0.2 (1) | 0.3 (2) | 0.3 (1) | -0.010 (7) |
| 8 | -0.02 (1) | 0 | 0.09 (9) | 0.3 (1) | 0.2 (1) | 0.3 (1) | 0.2 (2) | -0.009 (5) |
| 9 | -0.03 (1) | 0.2 (1) | 0.1 (3) | 0.29 (9) | 0.2 (3) | 0.5 (2) | 0.2 (2) | -0.03 (2) |
| 10 | -0.019 (9) | na | 0.1 (1) | na | 0 | na | 0.4 (3) | -0.03 (2) |
| 11 | 1.8 (9) | na | 1.9 (6) | na | 3.3 (6) | na | 6 (2) | 3.5 (8) |
| 12 | -0.02 (1) | na | -0.01 (1) | na | 0.3 (3) | na | 0.7 (5) | -0.03 (1) |
| 13 | 0.8 (2) | na | 0.7 (4) | na | 1.4 (3) | na | 4 (1) | 1.8 (5) |
| 14 | -0.007 (3) | na | 0.2 (1) | na | 0.4 (2) | na | 0.8 (8) | 0.3 (3) |
| 15 | -0.049 (9) | 0.14 (8) | 0.03 (3) | 0.4 (1) | 0.01 (1) | 0.6 (3) | 0.08 (3) | -0.05 (2) |
| p$^a$ | -0.03 (2) | 0.01 (1) | 0.1 (3) | 0.20 (6) | 0.04 (4) | 0.09 (5) | 0.11 (9) | -0.03 (2) |

$^a$ pure PEDOT-PSS
*Standard deviations for the last digit of the values are given in parentheses

FIG. 5A

Average % $\Delta R_{max}/R_b$ values for PEDOT-PSS detectors upon exposure to 16 different analytes at 5% of their vapor pressure

| Detector | TFMBenzene | Benzaldehyde | Acetone | Ethanol | Methanol | Nitrobenzene | Acetonitrile | Nitromethane |
|---|---|---|---|---|---|---|---|---|
| 1 | 0.1 (1) | 0.17 (8) | 0.5 (2) | 2.1 (4) | 5.6 (3) | 0.08 (5) | 1.4 (1) | 1.2 (1) |
| 2 | 0.2 (3) | 0.3 (2) | 0.8 (4) | 3.6 (5) | 9.6 (6) | 0.2 (1) | 2.3 (4) | 2.1 (5) |
| 3 | 0.3 (2) | 0.3 (2) | 0.76 (9) | 1.5 (2) | 1.6 (3) | 0.2 (1) | 2.0 (1) | 2.3 (3) |
| 4 | 0.2 (2) | 0.3 (2) | 0.8 (3) | 3.3 (6) | 8.1 (8) | 0.1 (1) | 2.5 (2) | 2.0 (2) |
| 5 | 0.2 (1) | 0.3 (1) | 0.7 (2) | 2.5 (6) | 6.2 (8) | 0.2 (1) | 1.9 (3) | 1.5 (3) |
| 6 | 0.1 (1) | 0.2 (1) | 0.5 (2) | 1.6 (3) | 3.9 (4) | 0.09 (7) | 1.5 (2) | 1.2 (2) |
| 7 | 0.2 (2) | 0.3 (2) | 0.9 (4) | 3.3 (4) | 7.4 (5) | 0.1 (1) | 2.5 (3) | 2.0 (3) |
| 8 | 0.2 (2) | 0.2 (1) | 0.8 (2) | 2.5 (4) | 6.0 (6) | 0.11 (8) | 2.0 (2) | 1.7 (2) |
| 9 | 0.2 (2) | 0.3 (2) | 0.7 (3) | 3.1 (3) | 12 (1) | 0.18 (9) | 2.6 (2) | 2.1 (2) |
| 10 | na | na | 0.8 (4) | 3.1 (9) | 11 (2) | na | na | na |
| 11 | na | na | 9.4 (9) | 14 (2) | 17 (2) | na | na | na |
| 12 | na | na | 1.4 (8) | 5.7 (1) | 14 (2) | na | na | na |
| 13 | na | na | 6.3 (6) | 9 (1) | 12 (1) | na | na | na |
| 14 | na | na | 1.7 (8) | 5.5 (8) | 11 (2) | na | na | na |
| 15 | 0.2 (2) | 0.23 (6) | 0.38 (5) | 1.49 (9) | -0.105 (7) | 0.15 (5) | -0.06 (2) | 1.50 (9) |
| P[a] | 0.03 (3) | 0.14 (4) | 0.5 (1) | 2.7 (7) | 11 (1) | 0.09 (3) | 1.1 (4) | 1.8 (3) |

[a] pure PEDOT-PSS
*Standard deviations for the last digit of the values are given in parentheses

FIG. 5B

Table 4: Resolution factors calculated using an array of 9 different PEDOT-PSS composite detectors

| | Benzene | Toluene | MethoxyBenzene | Chloroform | Chlorobenzene | EtOAc | THF |
|---|---|---|---|---|---|---|---|
| Hexane | 4.3 | 4.7 | 10.0 | 6.6 | 3.6 | 16.0 | 2.0 |
| Benzene | | 3.2 | 3.1 | 5.2 | 2.6 | 3.7 | 5.0 |
| Toluene | | | 4.8 | 4.0 | 3.1 | 4.4 | 4.9 |
| MethoxyBenzene | | | | 11 | 3.5 | 6.0 | 14 |
| Chloroform | | | | | 4.3 | 10 | 5.7 |
| Chlorobenzene | | | | | | 4.0 | 3.8 |
| EtOAc | | | | | | | 14 |
| THF | | | | | | | |
| TFMbenzene | | | | | | | |
| Benzaldehyde | | | | | | | |
| Acetone | | | | | | | |
| Ethanol | | | | | | | |
| Methanol | | | | | | | |
| Nitrobenzene | | | | | | | |
| Acetonitrile | | | | | | | |

FIG. 6A

Table 4: Resolution factors calculated using an array of 9 different PEDOT-PSS composite detectors

| | TFMbenzene | Benzaldehyde | Acetone | Ethanol | Methanol | Nitrobenzene | Acetonitrile | Nitromethane |
|---|---|---|---|---|---|---|---|---|
| Hexane | 4.6 | 9.3 | 42 | 58 | 360 | 7.2 | 130 | 51 |
| Benzene | 1.6 | 1.7 | 11 | 27 | 147 | 2.3 | 88 | 32 |
| Toluene | 2.6 | 3.3 | 27 | 44 | 59 | 4.5 | 33 | 35 |
| MethoxyBenzene | 4.9 | 2.3 | 6.6 | 23 | 83 | 2.6 | 62 | 24 |
| Chloroform | 3.0 | 5.5 | 22 | 37 | 78 | 7.7 | 36 | 32 |
| Chlorobenzene | 2.3 | 3.7 | 6.8 | 16 | 144 | 2.6 | 50 | 12 |
| EtOAc | 2.5 | 4.3 | 32 | 47 | 75 | 4.6 | 24 | 29 |
| THF | 7.9 | 7.4 | 37 | 62 | 240 | 6.4 | 280 | 52 |
| TFMbenzene | - | 1.9 | 42 | 58 | 360 | 2.7 | 130 | 51 |
| Benzaldehyde | - | - | 6.0 | 27 | 86 | 3.4 | 20 | 23 |
| Acetone | - | - | - | 24 | 71 | 6.3 | 26 | 24 |
| Ethanol | - | - | - | - | 49 | 25 | 14 | 14 |
| Methanol | - | - | - | - | - | 120 | 66 | 77 |
| Nitrobenzene | - | - | - | - | - | - | 38 | 37 |
| Acetonitrile | - | - | - | - | - | - | - | 20 |

FIG. 6B

Table 5: Average % $\Delta R_{max}/R_b$ values for carbon black composite detectors upon exposure to 16 different analytes at 5% of their vapor pressure

| Detector | Hexane | Benzene | Toluene | Methoxybenzene | Chloroform | Chlorobenzene | Ethyl Acetate | THF |
|---|---|---|---|---|---|---|---|---|
| 1 | 0.2 (2) | 0.4 (1) | 0.3 (2) | 0.3 (1) | 1.0 (3) | 0.3 (5) | 0.54 (8) | 0.49 (7) |
| 2 | 0.49 (7) | 0.79 (4) | 0.8 (2) | 1.43 (6) | 0.6 (1) | 0.96 (5) | 0.63 (8) | 0.8 (1) |
| 3 | 1.4 (3) | 2.4 (8) | 2.7 (6) | 4 (2) | 6 (1) | 4 (1) | 1.6 (2) | 2.1 (4) |
| 4 | 2.0 (6) | 2.7 (3) | 2.7 (7) | 2.1 (3) | 6.0 (7) | 2.5 (3) | 3.4 (4) | 3.9 (3) |
| 5 | 7 (2) | 11 (2) | 11 (3) | 12 (2) | 21 (8) | 14 (2) | 6 (1) | 9 (2) |
| 6 | 0.9 (2) | 1.5 (1) | 1.5 (2) | 2.3 (2) | 1.8 (2) | 2.2 (1) | 0.80 (4) | 1.02 (8) |
| 7 | 0.4 (3) | 0.8 (4) | 0.7 (3) | 0.7 (4) | 1.4 (8) | 0.8 (3) | 1.0 (5) | 1.1 (6) |
| 8 | 0.3 (3) | 0.1 (1) | 0.4 (3) | 0.4 (6) | 0.8 (3) | 0.2 (1) | 0.9 (3) | 1.1 (4) |
| 9 | 0.1 (1) | 0.08 (6) | 0.2 (2) | 1 (3) | 0.3 (2) | 0.08 (5) | 0.4 (2) | 0.21 (7) |

| Detector | TFMBenzene | Benzaldehyde | Acetone | Ethanol | Methanol | Nitrobenzene | Acetonitrile | Nitromethane |
|---|---|---|---|---|---|---|---|---|
| 1 | 0.11 (4) | 0.22 (5) | 0.76 (5) | 0.46 (6) | 0.62 (4) | 0.22 (5) | 1.03 (3) | 1.4 (3) |
| 2 | 0.63 (7) | 1.07 (5) | 0.54 (3) | 0.14 (5) | 0.16 (5) | 1.16 (7) | 0.25 (5) | 0.23 (6) |
| 3 | 1.9 (7) | 3 (1) | 1.5 (3) | 1.3 (2) | 1.5 (3) | 4 (2) | 1.6 (5) | 2.3 (8) |
| 4 | 1.4 (3) | 1.6 (4) | 3.0 (3) | 2.4 (3) | 2.5 (3) | 1.4 (3) | 1.9 (3) | 1.8 (2) |
| 5 | 11 (2) | 7.6 (5) | 4.2 (8) | 1.7 (4) | 1.3 (3) | 9.1 (4) | 2.3 (4) | 3.0 (5) |
| 6 | 1.3 (1) | 2.1 (1) | 0.69 (3) | 0.37 (3) | 0.38 (3) | 2.5 (1) | 0.55 (9) | 0.7 (1) |
| 7 | 0.4 (1) | 0.7 (3) | 1.3 (7) | 0.6 (3) | 0.9 (2) | 0.7 (3) | 1.6 (6) | 1.6 (6) |
| 8 | 0.09 (9) | 0.2 (1) | 2.6 (5) | 2.5 (5) | 3.5 (5) | 0.1 (1) | 2.7 (7) | 1.7 (2) |
| 9 | 0.05 (3) | 0.12 (7) | 0.8 (2) | 1.7 (3) | 5.0 (9) | 0.11 (6) | 2.0 (3) | 1.5 (3) |

*Standard deviations for the last digit of the values are given in parentheses

FIG. 7

Average %ΔR/R and %Δf/f' for 10 exposures of carbon black and PEDOT-PSS composite detectors to four analytes at 5% of each analyte's vapor pressure. Standard deviations for the last digit of the values are given in parenthesis.

| | Poly(vinyl butyral) | | | | Poly(2-hydroxyethylmethacrylate) | | | |
|---|---|---|---|---|---|---|---|---|
| | Carbon Black | | PE-DOT PSS | | Carbon Black | | PE-DOT PSS | |
| | ΔR/R | Δf/f' | ΔR/R | Δf/f' | ΔR/R | Δf/f' | ΔR/R | Δf/f' |
| Acetone | 3.2 (5) | -1.2 (1) | 1 (2) | -0.4 (1) | 1.8 (4) | -2.4 (7) | 0.7 (4) | -0.3 (1) |
| Methanol | 1.7 (2) | -0.62 (7) | 14 (2) | -0.95 (9) | 5.6 (7) | -1.3 (2) | 17 (2) | -1.35 (6) |
| THF | 4.7 (4) | -1.59 (8) | -0.2 (2) | -0.31 (4) | 0.5 (1) | -0.8 (2) | -0.4 (4) | -0.08 (2) |
| Toluene | 3.0 (4) | -1.20 (6) | 0.3 (2) | -0.22 (4) | 0.05 (7) | -0.2 (4) | -0.2 (2) | -0.06 (1) |

FIG. 9

Resolution factors calculated using an array of 9 different carbon black composite detectors

| | Benzene | Toluene | MethoxyBenzene | Chloroform | Chlorobenzene | EtOAc | THF |
|---|---|---|---|---|---|---|---|
| Hexane | 7.0 | 4.0 | 12 | 11 | 10 | 6.2 | 6.7 |
| Benzene | - | 7.9 | 15 | 12 | 30 | 35 | 11 |
| Toluene | - | - | 7.9 | 8.1 | 14 | 7.9 | 5.2 |
| MethoxyBenzene | - | - | - | 15 | 20 | 28 | 17 |
| Chloroform | - | - | - | - | 21 | 21 | 9.0 |
| Chlorobenzene | - | - | - | - | - | 51 | 20 |
| EtOAc | - | - | - | - | - | - | 5.2 |
| THF | - | - | - | - | - | - | - |
| TFMbenzene | - | - | - | - | - | - | - |
| Benzaldehyde | - | - | - | - | - | - | - |
| Acetone | - | - | - | - | - | - | - |
| Ethanol | - | - | - | - | - | - | - |
| Methanol | - | - | - | - | - | - | - |
| Nitrobenzene | - | - | - | - | - | - | - |
| Acetonitrile | - | - | - | - | - | - | - |

FIG. 13A

Resolution factors calculated using an array of 9 different carbon black composite detectors

| | TFMbenzene | Benzaldehyde | Acetone | Ethanol | Methanol | Nitrobenzene | Acetonitrile | Nitromethane |
|---|---|---|---|---|---|---|---|---|
| Hexane | 8.5 | 11 | 11 | 18 | 19 | 13 | 100 | 30 |
| Benzene | 20 | 28 | 37 | 89 | 70 | 26 | 71 | 49 |
| Toluene | 11 | 11 | 12 | 16 | 26 | 12 | 27 | 25 |
| MethoxyBenzene | 19 | 25 | 39 | 56 | 54 | 17 | 71 | 73 |
| Chloroform | 23 | 17 | 37 | 24 | 38 | 18 | 27 | 18 |
| Chlorobenzene | 21 | 31 | 60 | 120 | 110 | 30 | 92 | 49 |
| EtOAc | 24 | 42 | 10 | 30 | 35 | 28 | 41 | 33 |
| THF | 20 | 18 | 14 | 24 | 31 | 19 | 22 | 21 |
| TFMbenzene | - | 18 | 41 | 49 | 58 | 21 | 47 | 31 |
| Benzaldehyde | - | - | 46 | 94 | 57 | 5.2 | 46 | 38 |
| Acetone | - | - | - | 18 | 33 | 34 | 19 | 24 |
| Ethanol | - | - | - | - | 14 | 50 | 17 | 33 |
| Methanol | - | - | - | - | - | 34 | 21 | 24 |
| Nitrobenzene | - | - | - | - | - | - | 35 | 30 |
| Acetonitrile | - | - | - | - | - | - | - | 21 |

FIG. 13B

Summary of pairwise resolution factors for unnormalized, normalized, and randomly combined arrays. Detectors 1-9 are carbon black composites, and detectors 10-18 are the respective PEDOT-PSS composites.

| Detectors (1-9) Carbon Black (10-18) PEDOT-P | | | | | | | | | | (across all 16 analyte pairs) | | | | (polar vs. polar) | | | (polar vs. nonpolar) | | | (nonpolar vs. nonpolar) | | |
|---|---|---|---|---|---|---|---|---|---|---|---|---|---|---|---|---|---|---|---|---|---|---|
| | 2 | 3 | 4 | 5 | 6 | 7 | 8 | 9 | | MAX | MIN | AVG | STDE | MAX | MIN | AVG | MAX | MIN | AVG | MAX | MIN | AVG |
| 1 | 11 | 12 | 13 | 14 | 15 | 16 | 17 | 18 | | | | | | | | unnormalized | | | | | | |
| 1 | 11 | 12 | 13 | 14 | 15 | 16 | 17 | 18 | | 120 | 4.0 | 30 | 22 | 94 | 14 | 34 | 120 | 10 | 37 | 51 | 4.0 | 16 |
| 10 | | | | | | | | | | 360 | 1.6 | 33 | 53 | 120 | 6.0 | 39 | 360 | 1.7 | 47 | 16 | 1.6 | 5.5 |
| | | | | | | | | | | | | | | | | normalized | | | | | | |
| 1 | 2 | 3 | 4 | 5 | 6 | 7 | 8 | 9 | | 82 | 2.4 | 25 | 16 | 52 | 11 | 29 | 82 | 8.9 | 31 | 43 | 2.4 | 14 |
| 10 | 11 | 12 | 13 | 14 | 15 | 16 | 17 | 18 | | 45 | 1.3 | 7.0 | 7.1 | 32 | 2.9 | 13 | 45 | 1.6 | 7.6 | 6.1 | 1.3 | 2.6 |
| | | | | | | | | | | | | | | random combinations, normalized | | | | | | | | |
| 15 | 8 | 4 | 11 | 3 | 6 | 10 | 16 | 12 | | 170 | 1.6 | 25 | 26 | 170 | 8.2 | 39 | 140 | 2.8 | 29 | 24 | 1.6 | 9.4 |
| 9 | 2 | 15 | 1 | 13 | 7 | 4 | 10 | 5 | | 72 | 1.9 | 20 | 14 | 60 | 10 | 28 | 72 | 7.6 | 23 | 31 | 1.9 | 11 |
| 16 | 4 | 3 | 18 | 11 | 5 | 12 | 9 | 8 | | 81 | 1.9 | 19 | 14 | 56 | 10 | 23 | 81 | 6.7 | 23 | 30 | 1.9 | 10 |
| 12 | 17 | 4 | 10 | 13 | 18 | 3 | 14 | 15 | | 1100 | 1.7 | 38 | 110 | 120 | 8.0 | 34 | 1100 | 3.0 | 57 | 15 | 1.7 | 6.8 |
| 7 | 17 | 4 | 2 | 10 | 1 | 16 | 9 | 13 | | 84 | 1.7 | 17 | 13 | 51 | 9.5 | 21 | 84 | 6.5 | 22 | 23 | 1.7 | 6.8 |
| 14 | 18 | 12 | 11 | 6 | 10 | 17 | 1 | 13 | | 230 | 1.4 | 22 | 30 | 68 | 12 | 30 | 230 | 1.4 | 29 | 13 | 1.5 | 4.9 |
| 4 | 8 | 16 | 14 | 12 | 13 | 2 | 11 | 6 | | 90 | 1.7 | 25 | 19 | 90 | 8.6 | 37 | 83 | 2.9 | 29 | 39 | 1.7 | 12 |
| 5 | 1 | 7 | 17 | 18 | 13 | 3 | 3 | 9 | | 160 | 2.0 | 32 | 36 | 110 | 10 | 37 | 160 | 6.9 | 46 | 14 | 2.0 | 6.8 |
| 15 | 1 | 16 | 4 | 3 | 14 | 17 | 2 | 7 | | 56 | 2.1 | 18 | 13 | 56 | 14 | 28 | 54 | 5.1 | 21 | 21 | 2.1 | 8.2 |
| 3 | 7 | 18 | 10 | 6 | 15 | 2 | 9 | 13 | | 61 | 1.8 | 17 | 12 | 55 | 12 | 28 | 61 | 2.3 | 19 | 29 | 1.8 | 8.4 |
| 3 | 17 | 10 | 13 | 7 | 5 | 16 | 18 | 12 | | 98 | 2.1 | 25 | 23 | 77 | 12 | 30 | 98 | 8.5 | 34 | 18 | 2.1 | 7.2 |
| 9 | 6 | 17 | 3 | 13 | 2 | 15 | 7 | 5 | | 80 | 1.9 | 23 | 15 | 45 | 10 | 25 | 80 | 8.4 | 29 | 36 | 1.9 | 12 |
| 14 | 2 | 13 | 9 | 17 | 4 | 4 | 18 | 7 | | 110 | 1.4 | 19 | 18 | 39 | 10 | 21 | 110 | 5.7 | 26 | 23 | 1.4 | 7.0 |
| 16 | 8 | 17 | 7 | 10 | 13 | 13 | 6 | 4 | | 69 | 2.0 | 19 | 14 | 64 | 10 | 27 | 69 | 5.3 | 23 | 30 | 2.0 | 9.1 |
| 5 | 9 | 12 | 8 | 6 | 14 | 3 | 17 | 4 | | 82 | 2.0 | 26 | 19 | 81 | 15 | 31 | 82 | 8.6 | 33 | 51 | 2.0 | 12 |
| 11 | 5 | 16 | 13 | 9 | 1 | 8 | 3 | 14 | | 150 | 1.6 | 28 | 37 | 130 | 6.6 | 36 | 150 | 5.0 | 39 | 11 | 1.6 | 4.4 |
| 6 | 10 | 7 | 13 | 3 | 10 | 9 | 12 | 8 | | 94 | 1.4 | 20 | 17 | 94 | 11 | 33 | 79 | 2.0 | 23 | 17 | 1.6 | 7.0 |
| 8 | 5 | 16 | 2 | 11 | 1 | 8 | 7 | 18 | | 88 | 1.4 | 21 | 15 | 45 | 10 | 25 | 88 | 6.7 | 27 | 41 | 1.4 | 10 |
| 2 | 2 | 12 | 16 | 4 | 18 | 17 | 17 | 18 | | 77 | 1.2 | 17 | 11 | 41 | 10 | 21 | 77 | 5.9 | 22 | 22 | 1.2 | 7.1 |
| 9 | 3 | 15 | 12 | 11 | 1 | 14 | 4 | 10 | | 120 | 1.4 | 19 | 17 | 84 | 8.0 | 26 | 120 | 2.8 | 24 | 17 | 1.4 | 7.0 |
| | | | | Random Array AVG | | | | | | 150 | 1.7 | 22 | | 77 | 10 | 29 | 150 | 5.2 | 29 | 25 | 1.7 | 8.3 |
| | | | | Random Array MEDI | | | | | | 89 | 1.7 | 20 | | 66 | 10 | 28 | 83 | 5.5 | 26 | 23 | 1.7 | 7.7 |

FIG. 14

SENSORS OF CONDUCTING AND INSULATING COMPOSITES

CROSS REFERENCE TO RELATED APPLICATIONS

This application claims priority from Provisional Application Ser. No. 60/149,885, filed Aug. 18, 1999, to which application a priority claim is made under 35 U.S.C. §119 (e).

The U.S. Government has certain rights in this invention pursuant to Grant Nos. DAAK-60-97-K-9503 and DAAG-55-97-1-1087 awarded by the Army Research Office.

FIELD OF THE INVENTION

This invention relates generally to sensors and sensor systems for detecting analytes in samples, including environmental and biological samples, and, more particularly, to sensor systems that incorporate sensors having electrical properties that vary according to the presence and concentration of analytes, and to methods of using such sensor systems.

BACKGROUND

There is considerable interest in developing sensors that act as analogs of the mammalian olfactory system (Lundstrom et al., Nature 352:47–50, 1991; Shurmer and Gardner, Sens. Act. B 8:1–11, 1992; Shurmer and Gardner, Sens. Actuators B 15:32, 1993). In practice, most chemical sensors suffer from some interference by responding to chemical species that are structurally or chemically similar to the desired analyte. This interference is an inevitable consequence of the "lock" being able to fit a number of imperfect "keys". Such interferences limit the utility of such sensors to very specific situations.

Prior attempts to produce a broadly responsive sensor array have exploited heated metal oxide thin film resistors (Gardner et al., Sens. Act. B4:117–121, 1991; Gardner et al., Sens. Act. B 6:71–75, 1991), polymer sorption layers on the surfaces of acoustic wave resonators (Grate and Abraham, Sens. Act. B 3:85–111, 1991; Grate et al., Anal. Chem. 65:1868–1891, 1993), arrays of electrochemical detectors (Stetter et al., Anal. Chem. 58:860–866, 1986; Stetter et al., Sens. Act. B:143–47, 1990; Stetter et al., Anal. Chem. Acta284:1–11, 1993), conductive polymers or composites that consist of regions of conductors and regions of insulating organic materials (Pearce et al., Analyst 118:371–377, 1993; Shurmer et al., Sens. Act. B4:29–33, 1991; Doleman et al., Anal. Chem. 70:2560–2654, 1998; Lonergan et al. Chem. Mater., 8:2298, 1996). Arrays of metal oxide thin film resistors, typically based on tin oxide ($SnO_2$) films that have been coated with various catalysts, yield distinct, diagnostic responses for several vapors (Corcoran et al., Sens. Act. B 15:32–37, 1993). However, due to the lack of understanding of catalyst function, $SnO_2$ arrays do not allow deliberate chemical control of the response of elements in the arrays nor reproducibility of response from array to array. Surface acoustic wave resonators are extremely sensitive to both mass and acoustic impedance changes of the coatings in array elements, but the signal transduction mechanism involves somewhat complicated electronics, requiring frequency measurement to 1 Hz while sustaining a 100 MHZ Rayleigh wave in the crystal. Attempts have also been made to construct arrays of sensors with conducting organic polymer elements that have been grown electrochemically through use of nominally identical polymer films and coatings. Moreover, Pearce et al., Analyst 118:371–377, 1993; and Gardner et al., Sensors and Actuators B 18–19:240–243, 1994, describe, polypyrrole based sensor arrays for monitoring beer flavor. Shurmer (1990) U.S. Pat. No. 4,907,441, describes general sensor arrays with particular electrical circuitry. U.S. Pat. No. 4,674,320 describes a single chemoresistive sensor of a semi-conductive material selected from the group consisting of phthalocyanine, halogenated phthalocyanine and sulfonated phthalocyanine, which was used to detect a gas contaminant. Other gas sensors have been described by Dogan et al, Synth. Met. 60:27–30, 1993; and Kukla, et al. Films. Sens. Act. B., Chemical 37:135–140, 1996.

Sensor arrays formed from a plurality of composites that consist of regions of a conductor and regions of an insulating organic material, usually an organic polymer as described in U.S. Pat. No. 5,571,401, have some advantages relative to the approaches described above, however there is a need for sensors and sensor materials that show dramatically improved detection sensitivity if the sensors and the sensing devices are to be as sensitive as the human olfactory system towards certain classes of compounds. The composites composed of conductors and insulating organic material have sensitivities that are primarily dictated by the swelling-induced sorption of a vapor into the composite material, and analytes that sorb to similar extents produce similar swellings and therefore produce similar detected signals (Doleman, et al., Proc. Natl. Acad. Sci. U.S.A, 95:5442–5447, 1998). However, the human nose shows greatly enhanced sensitivity towards certain classes of compounds such as, for example, biogenic amines and thiols than it does towards the corresponding chain-length alcohols or alkanes. This property is not displayed by composites that consist of regions of conductor and regions of a swellable insulator, whose swelling is similar for amines, thiols, alkanes, alcohols, and other materials of similar vapor pressure to each other. Certain odors have typically been missed by an electronic nose that is not responsive to such odors at least at the level comparable to a human, and such a device will not be acceptable to detect and classify odors that are perceived by humans or at levels that are desirable for food freshness, biomedical, disease state identification, and other applications. In addition, designing sensors that are particularly sensitive (i.e., more sensitive than the human olfactory system) can provide distinctive advantages in the detection and characterization of odors and their, biochemical properties.

Although the foregoing systems have some usefulness, there still remains a need in the art for a low cost, broadly responsive analyte detection sensor array based on a variety of sensors.

SUMMARY OF THE INVENTION

The present invention provides a sensor capable of identifying an analyte in a sample, and more particularly identifying polar and non-polar analytes in a sample. The sensor includes a composite of insulating material and a material that is a compositionally different material than the insulating material and has a temperature coefficient of resistance that is more positive than the insulating material. In one embodiment, the compositionally different material has a temperature coefficient of resistance that is more positive than the insulating material but less than the temperature coefficient of resistance of a metal such as Ag, Au, Cu, Pt, and AuCu. In another embodiment, the ratio of temperature coefficients of resistance of the compositionally different material to the insulator in a sensor is greater than 1.

In another embodiment, the artificial olfactory system (or electronic nose) uses an array of sensors to recognize an odorant. In such a configuration, the burden of recognition is not on highly specific receptors, as in the traditional "lock-and-key" molecular recognition approach to chemical sensing, but lies instead on the distributed pattern processing of the olfactory bulb and the brain.

The present invention fulfills this and other needs. It is therefore an object of the invention to provide a broadly responsive analyte detection sensor and sensor array based on a variety of "chemiresistor" elements. Such elements are simply prepared and are readily modified chemically to respond to a broad range of analytes. In addition, these sensors yield a rapid, low-power, dc electrical signal in response to the analyte of interest, and their signals are readily integrated with software- or hardware-based algorithms including neural networks for purposes of analyte identification.

In addition, the invention provides individual sensors that display enhanced sensitivity towards certain specific compounds of interest such as polar and non-polar analytes and other similar compounds. The sensor comprises regions of an electrically non-conductive or insulating material and regions of a material compositionally different than the non-conductive or insulating material having a temperature coefficient of resistance higher than the non-conductive material or insulator, wherein the sensor provides an electrical path through the regions of the non-conductive material and the compositionally different material, the sensors constructed to provide a first response when contacted with a first analyte and a second different response when contacted with a second different analyte. In one embodiment, the compositionally different material is selected from the group consisting of polyanilines, polypyrroles, polythiophenes, poly EDOTs (e.g., PEDOT-PSS) and derivatives thereof, and the non-conductive or insulating material is, for example, a material set forth in Table 2 below. These sensors can be used by themselves or in conjunction with other senior modalities (surface acoustic wave device, electrochemical gas sensors, etc.), or with sensors comprising conductive regions and insulating regions or conductive regions and non-conductive or semi-conductive regions to increase the performance and information content of a sensor array for detection of analytes in a sample.

In another embodiment, the present invention provides a sensor array comprising a plurality of sensors and a measuring apparatus, wherein the sensor are in communication with the measuring apparatus, at least one of the sensors comprising regions of a non-conductive or insulating material and regions of a material compositionally different than the non-conductive material, wherein said sensor provides an electrical path through the regions of the non-conductive material and the compositionally different material, the sensors constructed to provide a first response when contacted with a first analyte and a second, different response when contacted with a second different analyte. In one embodiment, at least one sensor in the array is comprised of compositionally different combinations of materials having regions of a non-conductive material and regions of a compositionally dissimilar material having a temperature coefficient of resistance more positive than the insulator. In another embodiment, the compositionally different material is selected from the group consisting of polyanilines, polypyrroles, polythiophenes, polyEDOTs, and derivatives thereof. In another embodiment, the compositionally different material has a temperature coefficient of resistance that is more positive than an insulator but less than a conductive metal such as, for example, Ag, Au, Cu, Pt, carbon black and AuCu.

BRIEF DESCRIPTION OF THE FIGURES

These and other objects of the present invention will now be described in detail with reference to the accompanying figures, in which:

FIG. 5 is a table that lists the relative differential resistance responses for all PEDOT-PSS detectors during exposure to each of sixteen different analytes.

FIG. 6 is a table that lists the resolution factors obtained for an array of nine PEDOT-PSS composites consisting of the first nine insulating polymers listed in FIG. 2.

FIG. 7 is a table that lists the relative differential resistance responses for these carbon black composite detectors upon exposure to each of sixteen different analytes.

FIG. 9 is a table showing the average % $\Delta R/R$ and % $\Delta f/f$ for 10 exposures of carbon black and PEDOT-PSS composite detectors to four analytes at 5% of each analyte's vapor pressure.

FIG. 13 is a table showing the resolution factors for a 9-detector carbon black composite array.

FIG. 14 is a table showing a summary of pairwise resolution factors for unnormalized, normalized and randomly combined arrays. Detectors 1–9 are carbon black composites, and detectors 10–18 are the respective PEDOT-PSS composites.

DETAILED DESCRIPTION OF THE INVENTION

Figure 1A:
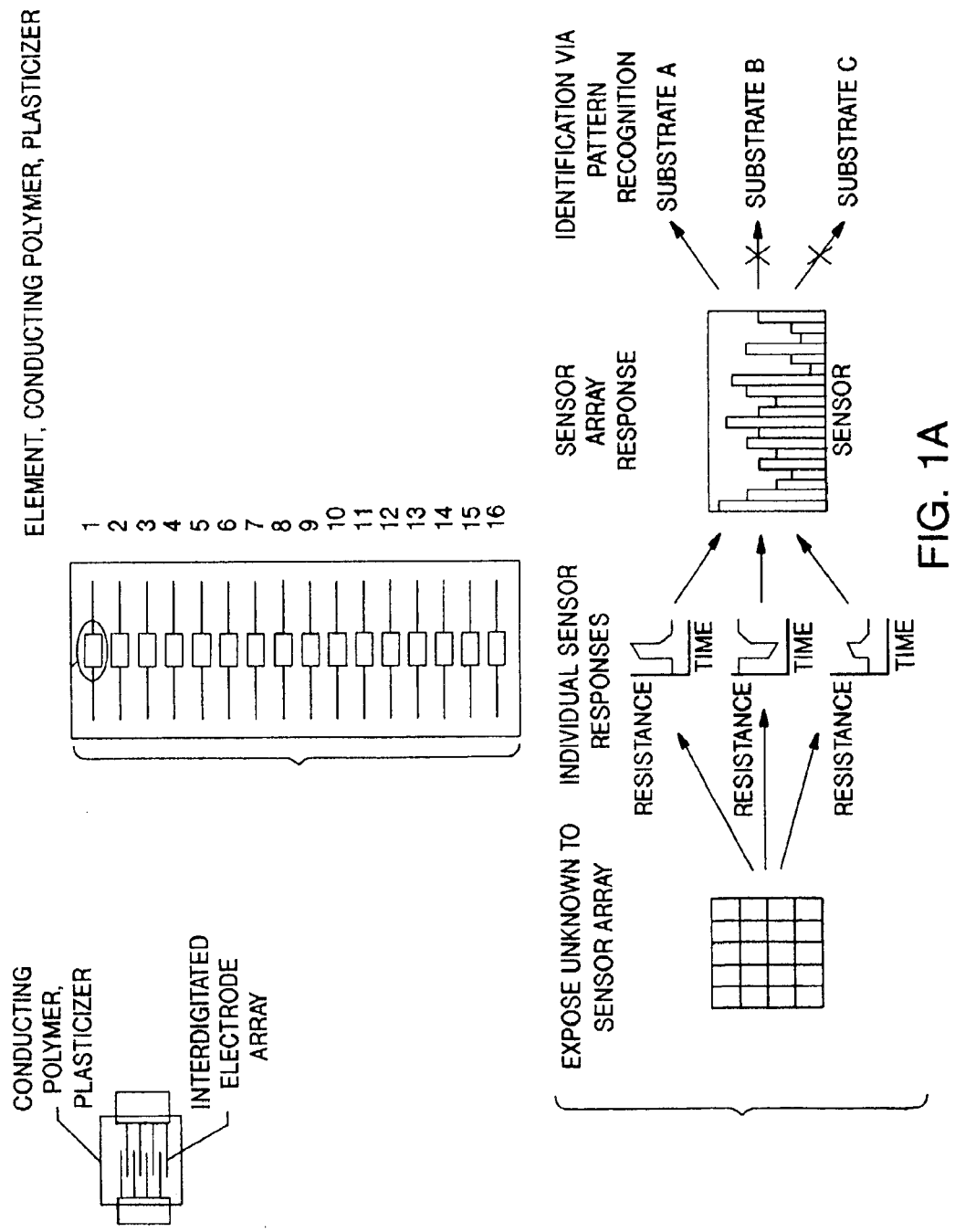
FIG. 1A shows a schematic of a typical sensor of the invention.

Intrinsically conductive polymers (e.g., polymers having a conductivity higher than insulators and non-conductive materials) are an attractive class of materials for use in sensor arrays. However, obtaining chemical diversity in intrinsically conductive polymers involves efforts, such as modification of the polymer backbone or modification of substituent groups. In addition, polymer backbones commonly used in intrinsically conductive polymers, such as polypyrrole and polythiophene, have electrical properties that are quite sensitive to humidity and to other environmental variations. Another approach is to use composites formed from a conducting material dispersed into a variety of insulating polymeric phases. Carbon black, Ag, Au, or some conducting organic polymers have all been used as the conductive phases in such composites (see, for example, U.S. Pat. No. 5,571,401, which is incorporated herein by reference). A wide variety of insulating polymers can be used as components of these types of detector elements, resulting in a chemically diverse set of resistive detectors having good vapor classification properties. One shortcoming of the carbon black composite preparations is that it is not straightforward to prepare composites using highly polar polymers because the hydrophobic carbon particles do not disperse well into polar media. In addition, the mean diameter of unagglomerated carbon black particles is approximately 20–50 nm, so that films of carbon black composites having thicknesses below 200 nm are difficult to prepare reproducibly and have not displayed good electrical resistance properties to date. In addition, it would be desirable to have detectors that show increased sensitivities towards polar compounds to improve the magnitude of the differences in response properties between polar and nonpolar detectors in an array. This would allow more robust analyte classification through the use of pattern recognition methods on the resulting data stream.

The sensors and sensor arrays disclosed herein act as an "electronic nose" to offer ease of use, speed, and identification of analytes and/or analyte regions all in a portable, relatively inexpensive implementation. Thus, a wide variety of analytes and fluids may be analyzed by the disclosed sensors, arrays and noses so long as the subject analyte is capable generating a detectable signal when it contacts a sensor of the invention or generating a differential response across a plurality of sensors of the array. Analyte applications include broad ranges of chemical classes such as organics including, for example, alkanes, alkenes, alkynes, dienes, alicyclic hydrocarbons, arenes, alcohols, ethers, ketones, aldehydes, carbonyls, carbanions, biogenic amines, thiols, polynuclear aromatics and derivatives of such organics, e.g., halide derivatives, etc., biomolecules such as sugars, isoprenes and isoprenoids, fatty acids and derivatives, and the like. Accordingly, commercial applications of the sensors, arrays and noses include environmental toxicology and remediation, biomedicine, materials quality control, food and agricultural products monitoring, anaesthetic detection, automobile oil or radiator fluid monitoring, breath alcohol analyzers, hazardous spill identification, explosives detection, fugitive emission identification, medical diagnostics, fish freshness, detection and classification of bacteria and microorganisms both in vitro and in vivo for biomedical uses and medical diagnostic uses, and the like. A wide variety of commercial applications are available for the sensor arrays and electronic noses including, but not limited to, heavy industrial manufacturing, ambient air monitoring, worker protection, emissions control, product quality testing, leak detection and identification, oil/gas petrochemical applications, combustible gas detection, $H_2S$ monitoring, hazardous leak detection and identification, emergency response and law enforcement applications, illegal substance detection and identification, arson investigation, enclosed space surveying, utility and power applications, emissions monitoring, transformer fault detection, food/beverage/agriculture applications, freshness detection, fruit ripening control, fermentation process monitoring and control applications, flavor composition and identification, product quality and identification, refrigerant and fumigant detection, cosmetic/perfume/fragrance formulation, product quality testing, personal identification, chemical/plastics/pharmaceutical applications, leak detection, solvent recovery effectiveness, perimeter monitoring, product quality testing, hazardous waste site applications, fugitive emission detection and identification, leak detection and identification, perimeter monitoring, transportation, hazardous spill monitoring, refueling operations, shipping container inspection, diesel/gasoline/aviation fuel identification, building/residential natural gas detection, formaldehyde detection, smoke detection, fire detection, automatic ventilation control applications (cooking, smoking, etc.), air intake monitoring, hospital/medical anesthesia & sterilization gas detection, infectious disease detection and breath applications, body fluids analysis, pharmaceutical applications, drug discovery and telesurgery. Another application for the sensor-based fluid detection device in engine fluids is an oil/antifreeze monitor, engine diagnostics for air/fuel optimization, diesel fuel quality, volatile organic carbon measurement (VOC), fugitive gases in refineries, food quality, halitosis, soil and water contaminants, air quality monitoring, leak detection, fire safety, chemical weapons identification, use by hazardous material teams, explosive detection, breathalyzers, ethylene oxide detectors and anaesthetics.

For example, the sensor and sensor arrays can be used to detect biogenic amines. Biogenic amines such as putrescine, cadaverine, and spermine are formed and degraded as a result of normal metabolic activity in plants, animals and microorganisms, and have been identified and quantified using analytical techniques such as gas chromatography-mass spectrometry (GC-MS), high performance liquid chromatography (HPLC) or array based vapor sensing in order to assess the freshness of foodstuffs such as meats (Veciananogues, 1997, J. Agr. Food Chem., 45:2036–2041), cheeses, alcoholic beverages, and other fermented foods. Additionally, aniline and o-toluidine have been reported to be biomarkers for patients having lung cancer (Preti et al., 1988, J. Chromat. Biomed. Appl.432:1–11), while dimethylamine and trimethylamine have been reported to be the cause of the "fishy" uremic breath odor experienced by patients with renal failure (Simenhoff, 1977, New England J. Med., 297:132–135). Thus, generally biogenic amines and thiols are biomarkers of bacteria, disease states, food freshness, and other odor-based conditions. Thus, the electronic nose sensor elements and arrays discussed herein incorporating these materials can be used to monitor the components in the headspace of urine, blood, sweat, and saliva of human patients, as well as breath, to diagnose various states of health and disease. In addition, they can be used for food quality monitoring, such as fish freshness (which involves volatile amine signatures), for environmental and industrial applications (oil quality, water quality, air quality and contamination and leak detection), for other biomedical applications, for law enforcement applications (breathalayzers), for confined space monitoring (indoor air quality, filter breakthrough, etc) and for other applications delineated above to add functionality and performance in an unanticipated fashion to existing sensor arrays though improvement in their properties by use in arrays that combine sensor modalities. For example, surface acoustic wave (SAW) arrays, quartz crystal microbalance arrays, composites consisting of regions of conductors and regions of insulators, bulk semi-conducting organic polymers, and other array types exhibit improved performance towards vapor discrimination and quantification when the sensors of the present invention are incorporated additionally into arrays that contain these other sensing modalities (e.g., wherein the array of sensors comprises a member selected from the group consisting of a metal oxide gas sensor, a conducting polymer sensor, a dye-impregnated polymer film on fiber optic detector, a polymer-coated micromirror, an electrochemical gas detector, a chemically sensitive field-effect transistor, a carbon black-polymer composite, a micro-electro- mechanical system device and a micro-opto-electro-mechanical system device).

Breath testing has long been recognized as a nonintrusive medical technique that might allow for the diagnosis of disease by linking specific volatile organic vapor metabolites in exhaled breath to medical conditions (see Table 1). In addition to breath analysis being nonintrusive, it offers several other potential advantages in certain instances, such as 1) breath samples are easy to obtain, 2) breath is in general a much less complicated mixture of components than either serum or urine samples, 3) direct information can be obtained on the respiratory function that is not readily obtainable by other means, and 4) breath analysis offers the potential for direct real time monitoring of the decay of toxic volatile substances in the body. Table 1 lists some of the volatile organic compounds that have been identified as targets for specific diseases using gas chromatography/mass spectrometry (GC/MS) methods, with emphasis on amines.

TABLE 1

| Patient Diagnosis | Target VOCs | VOC Source |
|---|---|---|
| Uremia; Preti, 1992; Simenhoff, 1977; Davies, 1997 | dimethylamine, trimethylamine | breath, urine |
| Trimethylaminuria; Preti, 1992; Alwaiz, 1989 | trimethylamine | breath, urine swat, vaginal discharge |
| Lung Cancer; Preti, 1992 | aniline, o-toluidine | lung air |
| Dysgeusia/Dysosmia; Preti, 1992; Oneill, 1988 | hydrogen sulfide, methyl mercaptn, pyridine, aniline, diphenylamine, dodecanol | lung air |
| Cystinuria; Manolis A., 1983, Clin. Chem. 29:5. | cadaverie, piperidine, putrescine, pyrrolidine | breath |
| Halitosis; Kozlovsky, 1994; Preti, 1992 | hydrogen sulfide, methyl mercaptan, cadaverine, putrescine, indole, skatole | mouth air |
| Bacterial Vaginosis; Chandiok, 1997, J. Clinical Path., 50:790. | amines | vaginal cavity and discharge |
| Liver cirrhosis Shimamoto, Hepato-gastroenterology 2000 Mar–Apr;47(32):443–5 | ammonia | blood; breath |

With reference now to the drawings, and particularly to FIG. 1A, there is shown a sensor array for detecting an analyte in a fluid for use in conjunction with an electrical measuring apparatus. The array comprises a plurality of differently responding sensors, at least one of the sensors comprising at least first and second conductive leads electrically coupled to and separated by a chemically sensitive resistor. The leads may be any convenient conductive material, usually a metal, and may be interdigitized to maximize signal-to-noise strength.

At least one sensor in the array is composed of a material comprising regions of an non-conductive or insulating material with regions of a compositionally dissimilar material that is electrically conductive. By an electrical conductor means that the material has a positive temperature coefficient of resistance. In one embodiment, the electrically conductive material has a temperature coefficient of resistance that is higher than the corresponding insulator or non-conductive material present on the sensor. In another embodiment, the electrically conductive material has a temperature coefficient that is less than that of inorganic metals such as Au, Ag, and Pt. In yet another embodiment, the electrically conductive material has a coefficient of resistance substantially similar to a polyEDOT, but excludes polypyrrole.

The resistor comprises a plurality of alternating regions of differing compositions and therefore differing conductivity transverse to the electrical path between the conductive leads. Generally, at least one of the sensors is fabricated by blending an insulator with a conductive material having a positive temperature coefficient of resistance. In one embodiment, the conductive material is poly(3,4-ethylenedioxy)thiophene-poly(styrene sulfonate) (PEDOT-PSS). For example, in a colloid, suspension or dispersion of particulate insulator or non-conductive material in a region of semi-conductive material (e.g., material having a temperature coefficient of resistance between the insulating material and an inorganic conductor), the regions separating the particles provide changes in conductance relative to the conductance of the particles themselves. The gaps of different conductance arising from the conductive material range in path length from about 10 to 1,000 angstroms, usually on the order of 100 angstroms. The path length and resistance of a given gap is not constant but rather is believed to change as the material absorbs, adsorbs or imbibes an analyte. Accordingly the dynamic aggregate resistance provided by these gaps in a given resistor is a function of analyte permeation of the conductive regions of the material. In some embodiments, the non-conductive or insulating material may also contribute to the dynamic aggregate resistance as a function of analyte permeation.

For example, Poly(3,4-ethylenedioxy)thiophene-poly(styrene sulfonate) (PEDOT-PSS) was used as the conductive component in a matrix of chemically different insulating polymers to form an array of vapor detectors. Such composites produced larger relative differential resistance responses when exposed to polar analytes than a corresponding carbon black filled polymer composite detectors. However, the PEDOT-PSS composites produced smaller responses than carbon black composites when exposed to nonpolar analytes. The PEDOT-PSS array exhibited better, on average, discrimination between pairs of polar analytes and polar/nonpolar analytes than did the carbon black composite array. Accordingly, the addition of PEDOT-PSS composites to an array of carbon black composite detectors therefore can produce improved overall discrimination of a vapor sensor system when used in tasks to differentiate between of a broad set of analyte vapors.

A wide variety of non-conductive or insulating, conductive, and semi-conductive materials can be used. In one embodiment, the insulating region (e.g., non-conductive region) can be anything that can impede electron flow from atom to atom, including, but not limited to, a material, a polymer, a plasticizer, an organic material, an organic polymer, a filler, a ligand, an inorganic material, a biomaterial, a solid, a liquid, a gas and the like. Table 2 provides examples of insulating materials that can be used for such purposes.

TABLE 2

| Major Class | Examples |
| --- | --- |
| Main-chain carbon polymers | poly(dienes), poly(alkenes), poly(acrylics), poly(methacrylics), poly(vinyl ethers), poly(vinyl thioethers), poly(vinyl alcohols), poly(vinyl ketones), poly(vinyl halides), poly(vinyl nitrites), poly(vinyl esters), poly(styrenes), poly(aryines), etc. |
| Main-chain acyclic hetervatom polymers | poly(oxides), poly(caronates), poly(esters), poly(anhydrides), poly(urethanes), poly(sulfonate), poly(siloxanes), poly(sulfides), poly(thioesters), poly(sulfones), poly(sulfonamindes), poly(amides), poly(ureas), poly(phosphazens), poly(silanes), poly(silazanes), etc. |
| Main-chain heterocyclic polymers | poly(furantetracarboxylic acid diimides), poly(benzoxazoles), poly(oxadiazoles), poly(benzothiazinophenothiazines), poly(benzothiazoles), poly(pyrazinoquinoxalines), poly(pyromenitimides), poly(quinoxalines), poly(benzimidazoles), poly(oxidoles), poly(oxoisinodolines), poly(diaxoisoindoines), poly(triazines), poly(pyridzaines), poly(pioeraziness), poly(pyridinees), poly(pioeridiens), poly(triazoles), poly(pyrazoles), poly(pyrrolidines), poly(carboranes), poly(oxabicyclononanes), poly(diabenzofurans), poly(phthalides), poly(acetals), poly(anhydrides), carbohydrates, etc. |

Nonconductive organic polymer materials; blends and copolymers; plasticized polymers; and other variations including those using the polymers listed here, may also be used. Combinations, concentrations, blend stoichiometries, percolation thresholds, and the like, are readily determined empirically by fabricating and screening prototype sensors (e.g., chemiresistors) as described below.

The other region of a sensor is typically comprised of a material that has a temperature coefficient of resistance greater than the non-conductive or insulating material (e.g., the ratio of conductivity of the second material to the non-conductive material is greater than 1). Examples of the second, dissimilar, material having a conductivity greater than the non-conductive material include polyaniline, polythiophene, polyEDOT, PEDOT-PSS and other conducting organic polymers such as those in the Handbook of Conducting Polymers (Handbook of Conducting Polymers, second ed., Marcel Dekker, New York 1997, vols. 1 & 2)). Other combinations of insulator/dissimilar material are also useful. In one implementation, the second dissimilar conductive material is PEDOT-PSS.

Table 3 provides exemplary conductive materials for use in sensor fabrication; blends, such as of those listed, may also be used. Typically conductors include, for example, those having a positive temperature coefficient of resistance. The sensors are comprised of a plurality of alternating regions of a non-conductive or insulating material with regions of a compositionally dissimilar material having a temperature coefficient of resistance greater than the non-conducting material. Without being bound to any particular theory, it is believed that the electrical pathway that an electrical charge traverses between the two contacting electrodes traverses the regions of dissimilar material.

TABLE 3

| Major Class | Examples |
| --- | --- |
| Organic Conductors | conducting polymers (poly(anilines), poly(thiophenes), poly(pyrroles), poly(aceylenes, etc.)), carbonaceous material (carbon blacks, graphite, coke, C60 etc.), charge transfer complexes (tetramethylparaphenylenediamine-chloranile, alkali metal tetracyanoquinodimethane complexes, tetrathiofulvalene halide complexes, etc.), etc. |
| Inorganic Conductors | metals and metal alloys (Ag, Au, Cu, Pt, AuCu alloy, etc.), highly doped semi-conductors (Si, GaAs, InP, MoS2, TiO2, etc.), conductive metal oxides (In2O3, SnO2, Na2Pt3O4, etc.), superconductors (Yba2Cu3O7, Ti2Ba2Ca2Cu3O10, etc.), etc. |
| Mixed inorganic/organic Conductor | Tetracyanoplatinate complexes, Iridium halocarbonyl complexes, stacked macrocyclic complexes. etc. |

In one embodiment, the region of the sensor having the higher conductivity is a material that can carry electrons from atom to atom. In certain embodiments, the material is a particle, such as a colloidal nanoparticle. As used herein the term "nanoparticle" refers to a conductive cluster, such as a metal cluster, having a diameter on the nanometer scale. Such nanoparticles are optionally stabilized with organic ligands. (Brust et al. can be used. (see, Brust, M.; Walker, M.; Bethell, D.; Schiffrin, D. J.; Whyman, R. J. Chem. Soc., Chem. Commun., 1994, 801–802.)

Table 4 provides exemplary of materials that can be used in the sensor and sensor arrays as a material having a conductivity greater than the non-conducting or insulating materials of Table 2.

TABLE 4

| | | |
| --- | --- | --- |
| a | (structure with R group) | R = alkyl, alkoxy |
| b | (thiophene structure with $R_1$, $R_2$) | $R_1$ = H, alkyl, alkoxy $R_2$ = H, alkyl, alkoxy |

TABLE 4-continued
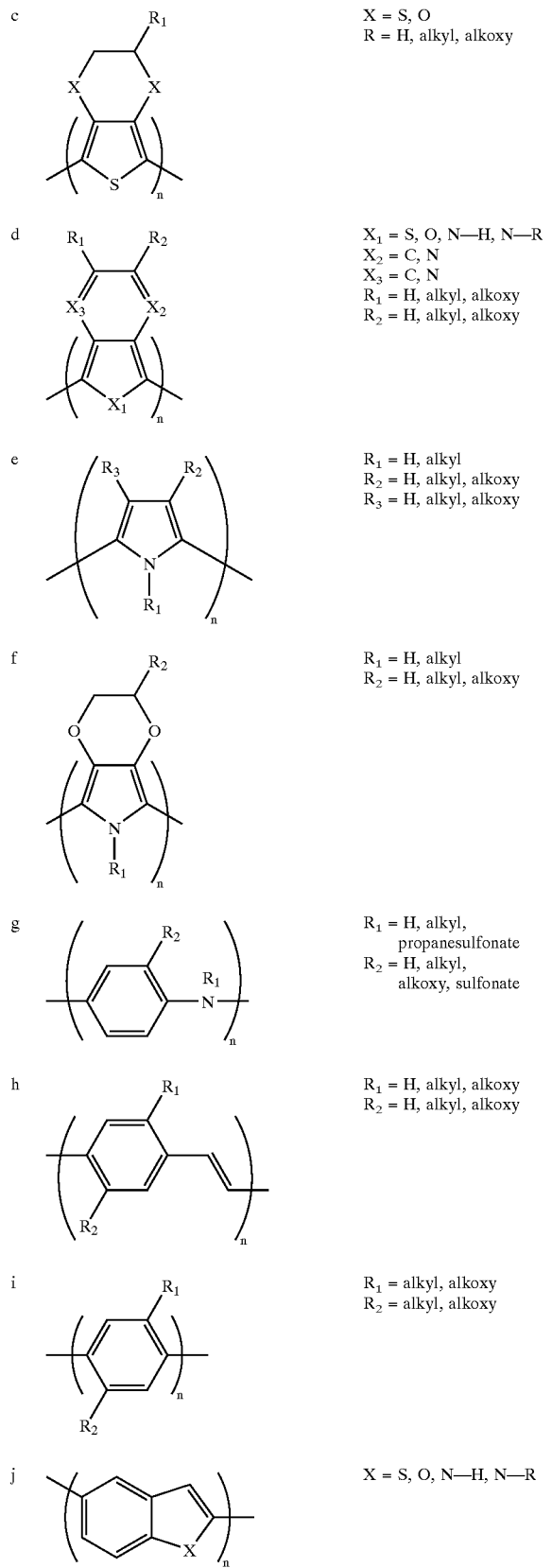
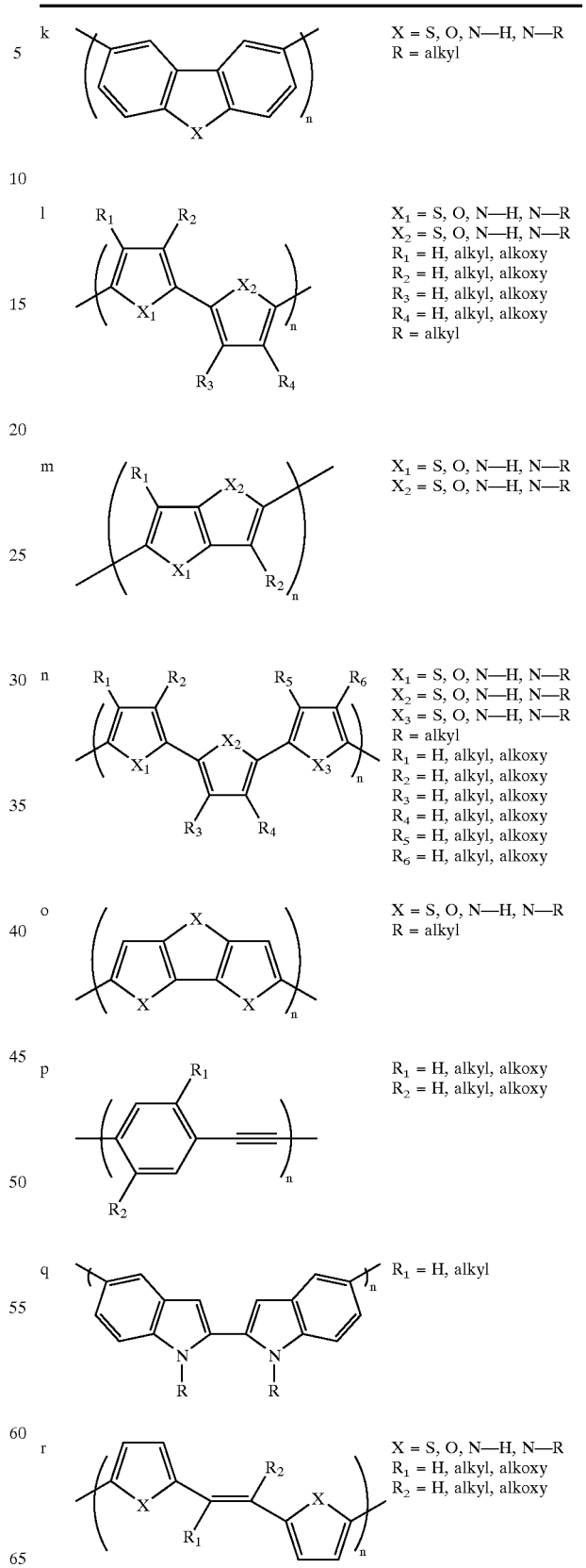

TABLE 4-continued

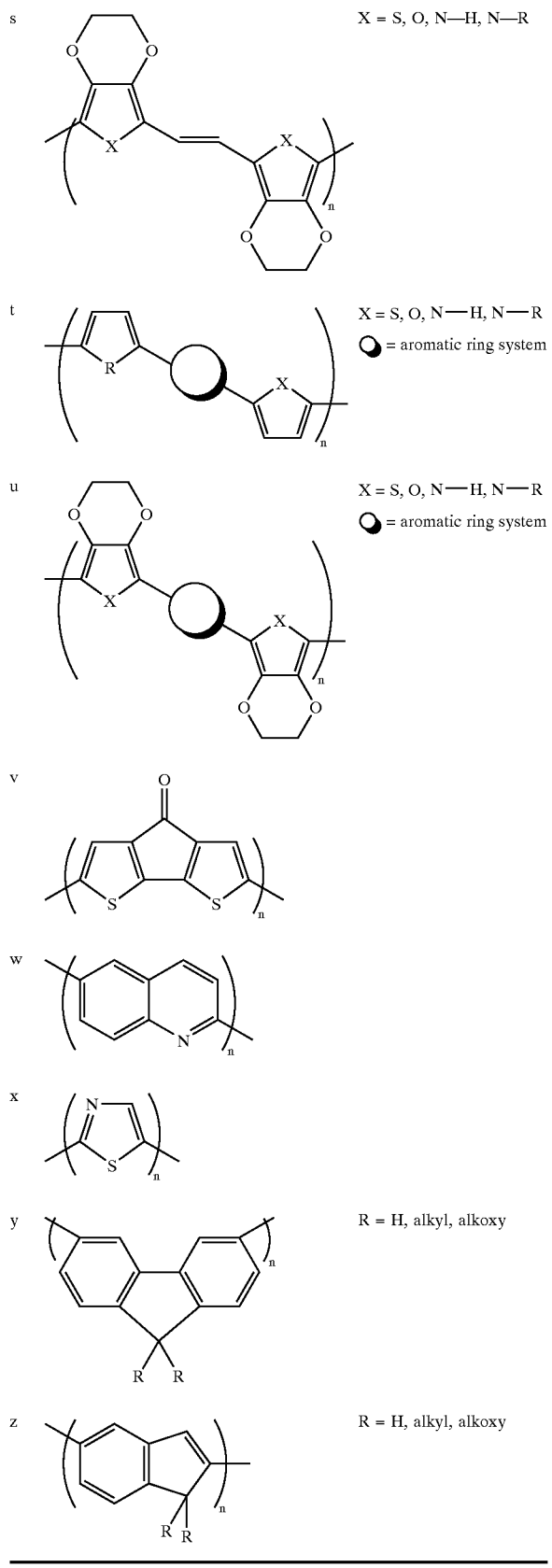

a. Poly(acetylene) and derivatives
b. Poly(thiophenes) and derivatives
c. Poly(3,4-ethylenedioxythiophene) and poly(3,4-ethylenedithiathiophene) and derivatives
d. Poly(isathianaphthene), poly(pyridothiophene), poly(pyrizinothiophene), and derivatives
e. Poly(pyrrole) and derivatives
f. Poly(3,4-ethylenedioxypyrrole) and derivatives
g. Poly(aniline) and derivatives
h. Poly(phenylenevinylene) and derivatives
i. Poly(p-phenylene) and derivatives
j. Poly(thianapthene), poly(benxofuran), and poly(indole) and derivatives
k. Poly(dibenzothiophene), poly(dibenxofuran), and poly(carbazole) and derivatives
l. Poly(bithiophene), poly(bifuran), poly(bipyrrole), and derivatives
m. Poly(thienothiophene), poly(thienofuran), poly(thienopyrrole), poly(furanylpyrrole), poly(furanylfuran), poly(pyrolylpyrrole), and derivatives
n. Poly(terthiophene), poly(terfuran), poly(terpyrrole), and derivatives
o. Poly(dithienothiophene), poly(difuranylthiophene), poly(dipyrrolylthiophene), poly(dithienofuran), poly(dipyrrolylfuran), poly(dipyrrolylpyrrole) and derivatives
p. Poly(phenyl acetylene) and derivatives
q. Poly(biindole) and derivatives
r. Poly(dithienovinylene), poly(difuranylvinylene), poly(dipyrrolylvinylene) and derivatives
s. Poly(1,2-trans(3,4-ethylenedinxythienyl)vinylene), poly(1,2-trans(3,4-ethylenedioxyfuranyl)vinylene), and poly(1,2-trans(3,4-ethylenedioxypyrrolyl)vinylene), and derivatives
t. The class of poly(bis-thienylarylenes) and poly(bis-pyrrolylarylenes) and derivatives
u. The class of poly(bis(3,4-ethylenedioxythienyl)arylenes) and derivatives
v. Poly(dithienylcyclopentenone)
w. Poly(quinoline)
x. Poly(thiazole)
y. Poly(fluorene) and derivatives
z. Poly(azulene) and derivatives Notes:
a. Aromatics=phenyl, biphenyl, terphenyl, carbazole, furan, thiophene, pyrrole, fluorene, thiazole, pyridine, 2,3,5,6-hexatluorobenzene, anthracene, coronene, indole, biindole, 3,4-ethylenedioxythiophene, 3,4-ethylenedioxypyrrole, and both the alkyl and alkoxy derivatives of these aromatics.
b. Alkyl=aliphatic group branched or straight chain ranging from $CH_3$ to $C_{20}H_{41}$.
c. Alkoxy=OR, where R is an aliphatic group that may either be branched or straight chain ranging from $CH_3$ to $C_{20}H_{41}$.
d. All conductive polymers are depicted in their neutral, nonconductive form. The polymers listed in the figure are doped oxidatively either by means chemically or electrochemically.
e. The class of polyanilines are acid doped and can be done so with a number of sulfonic acids including methane sulfonic acid, ethane sulfonic acid, propane sulfonic acid, butane sulfonic acid, pentane sulfonic acid, hexane sulfonic acid, heptane sulfonic acid, octane sulfonic acid, zionane sulfonic acid, decane sulfonic acid, dodecane sulfonic acid, dodecane sulfonic acid, dodecylbenzene-sulfonic acid, toluene sulfonic acid, benzene sulfonic acid, dinonanylnaphthalene sulfonic acid, and both the d and l forms of camphor sulfonic acid.

f. All other class of conductive polymers when doped there is an associated counter ion to compensate the positive charges on the backbone. These can be perchlorate, hexafluorophosphate, tetrafluoroborate, fluoride, chloride, bromide, iodide, triflate, etc.

The regions of the sensor having a conductivity greater than the non-conductive or insulating regions can be either an organic semi-conductor or organic conductor. "Semi-conductors" as used herein, include materials whose electrical conductivity increases as the temperature increases, whereas conductors are materials whose electrical conductivity decreases as the temperature increases. By this fundamental definition, the organic materials that are useful in the sensors of the present invention are either semi-conductors or conductors. Such materials produce a readily-measured resistance between two conducting leads separated by about 10 micron or more using readily-purchased multimeters having resistance measurement limits of 100 Mohm or less, and thus allow the passage of electrical current through them when used as elements in an electronic circuit at room temperature. The semi-conductors and conductors can be differentiated from insulators by their different room temperature electrical conductivity values. Insulators show very low room temperature conductivity values, typically less than about $10^{-8}$ ohm$^{-1}$ cm$^{-1}$. Poly(styrene), poly(ethylene), and other polymers elaborated in Table 2 provide examples of insulating organic materials. Metals have very high room temperature conductivities, typically greater than about 10 ohm$^{-1}$ cm$^{-1}$. Semi-conductors have conductivities greater than those of insulators, and are distinguished from metals by their different temperature dependence of conductivity, as described above. Examples of semi-conducting and conducting organic material are provided in Table 4. The materials that are useful in the sensors of the present invention are either electrical semi-conductors or conductors, and have room temperature electrical conductivities of greater than about $10^{-6}$ ohm$^{-1}$ cm$^{-1}$, preferably having a conductivity of greater than about $10^{-3}$ ohm$^{-1}$ cm$^{-1}$.

Accordingly, the sensors of the present invention include sensors comprising regions of a non-conductive or insulating material and regions of a material that is an electrical conductor or semi-conductor (i.e., having a conductivity greater than the non-conductive or insulating material.

The chemiresistors can be fabricated by many techniques such as, but not limited to, solution casting, suspension casting, and mechanical mixing. In general, solution cast routes are advantageous because they provide homogeneous structures and ease of processing. With solution cast routes, sensor elements may be easily fabricated by spin, spray or dip coating. Since all elements of the sensor film must be soluble, however, solution cast routes are somewhat limited in their applicability. Suspension casting still provides the possibility of spin, spray or dip coating but more heterogeneous structures than with solution casting are expected. With mechanical mixing, there are no solubility restrictions since it involves only the physical mixing of the resistor components, but device fabrication is more difficult since spin, spray and dip coating are no longer possible. A more detailed discussion of each of these follows.

For systems where both the insulating and compositionally dissimilar conducting material or their reaction precursors are soluble in a common solvent, the chemiresistors can be fabricated by solution casting. The oxidation of pyrrole by phosphomolybdic acid is an example of such a system. In this reaction, the phosphomolybdic acid and pyrrole are dissolved in tetrahydrofuran (THF) and polymerization occurs upon solvent evaporation. This allows for THF soluble compositionally different conductive, semi-conductive, and non-conductive materials to be dissolved into this reaction region thereby allowing the composite to be formed in a single step upon solvent evaporation.

A variety of permutations on this scheme are possible for other conducting polymers. Some of these are listed below. Certain conducting polymers, such as substituted poly-(cyclooctatetraenes), are soluble in their undoped, non-conducting state in solvents such as THF or acetonitrile. Consequently, the blends between the undoped polymer and other organic materials can be formed from solution casting. After which, the doping procedure (exposure to $I_2$ vapor, for instance) can be performed on the blend to render the substituted poly(cyclooctatetraene) conductive.

Certain conducting polymers can also be synthesized via a soluble precursor polymer. In these cases, blends between the precursor polymer and the compositionally different material of the composite can first be formed followed by chemical reaction to convert the precursor polymer into the desired conducting polymer. For instance poly(p-phenylene vinylene) can be synthesized through a soluble sulfonium precursor. Blends between this sulfonium precursor and a non-conductive or conductive polymer can be formed by solution casting. After which, the blend can be subjected to thermal treatment under vacuum to convert the sulfonium precursor to the desired poly(p-phenylene vinylene).

In suspension casting, one or more of the components of the sensor is suspended and the others dissolved in a common solvent. Suspension casting is a rather general technique applicable to a wide range of species, which can be suspended in solvents by vigorous mixing or sonication. In one application of suspension casting, the conductive material or polymer is dissolved in an appropriate solvent (such as THF, acetonitrile, water, etc.). The non-conductive material is then suspended in this solution and the resulting region is used to dip coat or spray coat electrodes.

Mechanical mixing is suitable for all of the material combinations possible. In this technique, the materials are physically mixed in a ball-mill or other mixing device. For instance, conducting/insulating polymer composites are readily made by ball-milling. When the semi-conductive or conductive material can be melted or significantly softened without decomposition, mechanical mixing at elevated temperature can improve the mixing process. Alternatively, composite fabrication can sometimes be improved by several sequential heat and mix steps.

Once fabricated, the individual sensors can be optimized for a particular application by varying their chemical make up and morphologies. The chemical nature of the sensors determines to which analytes they will respond and their ability to distinguish different analytes. The relative ratio of non-conductive or insulating material to compositionally dissimilar conductive or semi-conductive material, along with the composition of any other components, can determine the specificity and magnitude of a response to a particular analyte since the resistance of the elements becomes more sensitive to sorbed molecules as the molecules interact chemically with the components of the composite that adsorb or absorb the analyte. The film morphology is also important in determining response characteristics. For instance, uniform thin films respond more quickly to analytes than do uniform thick ones. Hence, with an empirical catalogue of information on chemically diverse sensors made with varying ratios and amounts of semi-conductive, conducting, insulating or other material components and by differing fabrication routes, sensors can be chosen that are appropriate for the analytes expected in a particular application, their concentrations, and the desired response times. Further optimization can then be performed in an iterative fashion as feedback on the performance of an array under particular conditions becomes available.

In addition, the structural rigidity of the sensor (e.g., a chemiresistor) may be enhanced through a variety of techniques: chemical or radiation cross-linking of polymer components (dicumyl peroxide radical cross-linking, UV-radiation cross-linking of poly(olefins), sulfur cross-linking of rubbers, e-beam cross-linking of Nylon, and the like), the incorporation of polymers or other materials into the sensor to enhance physical properties (for instance, the incorporation of a high molecular weight, high melting temperature ($T_m$) polymers), the incorporation of the resistor elements into supporting matrices such as clays or polymer networks (forming the resistor blends within poly-(methylmethacrylate) networks or within the lamellae of montmorillonite, for instance). In another embodiment, the resistor is deposited as a surface layer on a solid matrix which provides means for supporting the leads. Typically, the matrix is a chemically inert, non-conductive substrate such as a glass or ceramic.

In addition, the sensor or sensor arrays of the invention can easily be integrated onto the front end of a simple amplifier interfaced to an A/D converter to efficiently feed the data stream directly into a neural network software or hardware analysis system. Such systems are useful for local and remote analysis of odors (see, for example, U.S. patent Ser. No. 09/596,758, filed Jun. 15, 2000, the disclosure of which is incorporated herein by reference).

Micro-fabrication techniques can integrate the sensor directly onto a micro-chip which contains the circuitry for analog signal conditioning/processing and then data analysis. This provides for the production of millions of incrementally different sensor elements in a single manufacturing step using ink-jet technology. Controlled compositional gradients in the sensor elements of a sensor array can be induced in a method analogous to how a color ink-jet printer deposits and mixes multiple colors. However, in this case rather than multiple colors, a plurality of different materials (e.g., non-conductive, insulating, conductive, semi-conductive materials, and the like) are suspended or dissolved in solution which can be deposited on a substrate. A sensor array of a million distinct elements only requires a 1 cm×1 cm sized chip employing lithography at the 10 micrometer feature level, which is within the capacity of conventional commercial processing and deposition methods. This technology permits the production of sensitive, small-sized, stand-alone chemical sensors.

In one embodiment, the sensor arrays have a predetermined inter-sensor variation in the structure or composition of the materials, for example, the conductive components and any insulating or plastizing components of the composites. The variation may be quantitative and/or qualitative. For example, the concentration, thickness or type of conductive or semi-conductive material and the concentration, thickness or type of insulator in the composite can be varied across sensors. The anions that accompany a particular material can be compositionally varied to add diversity to the array, as can the polymer composition itself, either structurally (through use of a different family of materials) or through modification of the backbone and/or side chains of the basic polymer structure. This ability to fabricate many chemically different materials allows ready incorporation of a wide range of chemical diversity into the sensor elements, and also allows facile control over the electrical properties of the sensor elements through control over the composition of an individual sensor element in the array.

Insulating materials such as commercial, off-the-shelf, organic polymers can provide the basic sensor components that respond differently to different analytes, based on the differences in polarity, molecular size, and other properties of the analyte in order to achieve the chemical diversity amongst array elements in the electronic nose sensors. Such insulators would include main-chain carbon polymers, main chain acyclic heteroatom polymers, main-chain heterocyclic polymers, and other insulating organic materials (see, for example, Table 2 above). Accordingly, the sensors in an array can readily be made by combinatorial methods in which a limited number of feedstocks is combined to produce a large number of chemically distinct sensor elements.

One method of enhancing the diversity of polymer based sensor or chemiresistor of the invention is through the use of polymer blends or copolymers (Doleman, et al. (1998) Anal. Chem. 70:2560–2654). Binary polymer blend sensors can be prepared from a variety of polymers at incrementally different blend stoichiometries. Instead of manually fabricating twenty blends of varying composition, a spray gun with dual controlled-flow feedstocks could be used to deposit a graded-composition polymer film across a series of electrodes. Such automated procedures allow extension of the sensor compositions beyond simple binary blends, thereby providing the opportunity to fabricate chemiresistors with sorption properties incrementally varied over a wide range. In the fabrication of many-component blends, a combinatorial approach aided by microjet fabrication technology is one approach that will be known to those skilled in the art. For instance, a continuous jet fed by five separate feedstocks can fabricate numerous polymer blends in a combinatorial fashion on substrates with appropriately patterned sets of electrodes. Multiple nozzle drop-on-demand systems (multiple nozzle continuous jet systems are not as prevalent because of their greater complexity) may also be used. In this approach, each nozzle would be fed with a different polymer, each dissolved in a common solvent. In this manner, a large number of combinations of 10–20 polymers can be readily fabricated.

The sensor and sensor arrays of the invention allow expanded utility because the signal for an imperfect "key" in one channel can be recognized through information gathered on another, chemically or physically dissimilar sensor or channel in the array. A distinct pattern of responses produced over the collection of sensors in the array can provide a fingerprint that allows classification and identification of the analyte, whereas such information would not have been obtainable by relying on the signals arising solely from a single sensor or sensing material (see, for example, PCT publication no. WO99/53300, the disclosure of which is incorporated herein by reference in its entirety).

The general method for using the disclosed sensors, arrays and electronic noses, for detecting the presence of an analyte in a sample, where the sample is, for example, a liquid, a gas or the headspace of a liquid, involves, in one embodiment, resistively sensing the presence of an analyte in a sample with a sensor comprising first and second conductive leads electrically coupled to and separated by a chemically sensitive resistor by measuring a detectable signal or change in resistance across the resistor in response to an analyte.

An ideal detector array would produce a unique signature (e.g., resistive fingerprint) for every different analyte to which it was exposed. Such a system, includes an array of sensors that probe important, but possibly subtle, molecular parameters such as chirality, and polarity. The term "chiral" is used herein to refer to an optically active or enantiomerically pure compound, or to a compound containing one or more asymmetric centers in a well-defined optically active configuration. Harnessing enantiomer resolution gives rise to myriad applications. For instance, because the active sites of enzymes are chiral, only the correct enantiomer is recognized as a substrate. Thus, pharmaceuticals having near enantiomeric purity are often many more times active than their racemic mixtures. However, many pharmaceutical formulations marketed today are racemic regions of the desired compound and its "mirror image." One optical form (or enantiomer) of a racemic region may be medicinally useful, while the other optical form may be inert or even harmful, as has been reported to be the case for thalidomide. Similarly other chemical-physical characteristics of an analyte can be measured including polarity. Accordingly, chiral sensor or polarity sensor elements could be part of a larger detector array that included non-chiral or non-polar elements, thus broadening the discrimination ability of such arrays. Accordingy, the sensor arrays of the invention provide the ability to detect chiral analytes and polar/non-polar analytes through their distinct response pattern on an array of sensors.

For example, Poly(3,4-ethylenedioxy)thiophene-poly (styrene sulfonate) (PEDOT-PSS) was used as the conductive component in a matrix of chemically different insulating polymers to form an array of vapor detectors. Such composites produced larger relative differential resistance responses when exposed to polar analytes than a corresponding carbon black filled polymer composite detectors. However, the PEDOT-PSS composites produced smaller responses than carbon black composites when exposed to nonpolar analytes. The PEDOT-PSS array exhibited better, on average, discrimination between pairs of polar analytes and polar/nonpolar analytes than did the carbon black composite array. Accordingly, the addition of PEDOT-PSS composites to an array of carbon black composite detectors therefore can produce improved overall discrimination of a vapor sensor system when used in tasks to differentiate between of a broad set of analyte vapors.

In addition, interpenetrating network (IPN) comprising a first polymer (e.g., a plasticizer) and a second polymer formed from an organic monomer polymerized in the presence of the first organic polymer can be formed. This technique works particularly well when dealing with polymers that are immiscible in one another, where the polymers are made from monomers that are volatile. Under these conditions, the preformed polymer is used to dictate the properties (e.g., viscosity) of the polymer-monomer region. Thus, the polymer holds the monomer in solution. Examples of such a system are (1) polyvinyl acetate with monomer methyl methacryl ate to form an IPN of pVA and pMMA, (2) pVA with monomer styrene to form an IPN of pVA and polystyrene, and (3) pVA with acrylonitrile to form an IPN of pVA and polyacrylonitrile. Each of the example compositions would be modified by the addition of an appropriate plasticizer. More than one monomer can be used where it is desired to create an IPN having one or more copolymers.

In another embodiment, the sensor for detecting the presence of a chemical analyte in a sample comprises a sensor of the invention electrically connected to an electrical measuring apparatus where the sensor is in thermal communication with a temperature control apparatus. In one embodiment, the sensor provides an electrical path through which electrical current may flow and a resistance (R) at a temperature (T) when contacted with a sample comprising a chemical analyte.

For example the sensor provides an electrical resistance ($R_m$) when contacted with a sample comprising a chemical analyte at a particular temperature ($T_m$). The electrical resistance observed may vary as the temperature varies, thereby allowing one to define a unique profile of electrical resistances at various different temperatures for any chemical analyte of interest. For example, a chemically sensitive resistor, when contacted with a sample comprising a chemical analyte of interest, may provide an electrical resistance $R_m$ at temperature $T_m$ where m is an integer greater than 1, and may provide a different electrical resistance $R_n$ at a different temperature $T_n$. The difference between $R_m$ and $R_n$ is readily detectable by an electrical measuring apparatus.

As such, a sensor or plurality of sensors in thermal communication with a temperature control apparatus allow one to vary the temperature at which electrical resistance is measured. If the sensor comprises an array of two or more chemically sensitive resistors each being in thermal communication with a temperature control apparatus, one may vary the temperature across the entire array (i.e., generate a temperature gradient across the array), thereby allowing electrical resistance to be measured simultaneously at various different temperatures and for various different sensor compositions. For example, in an array of chemically sensitive resistors, one may vary the composition of the resistors in the horizontal direction across the array, such that resistor composition in the vertical direction across the array remains constant. One may then create a temperature gradient in the vertical direction across the array, thereby allowing the simultaneous analysis of chemical analytes at different resistor compositions and different temperatures.

Methods for placing sensors in thermal communication with a temperature control apparatus are readily apparent to those skilled in the art and include, for example, attaching a heating or cooling element to the sensor and passing electrical current through said heating or cooling element. The temperature range across which electrical resistances may be measured will be a function of the sensor composition, for example the melting temperature of the sensor components, the thermal stability of the analyte of interest or any other component of the system, and the like. For the most part, the temperature range across which electrical resistance will be measured will be about 10° C. to 80° C., preferably from about 22° C. to about 70° C. and more preferably from about 20° C. to 65° C.

In yet another embodiment, rather than subjecting the sensor to a direct electrical current and measuring the electrical resistance through or across the sensor, the sensor can be subjected to an alternating electrical current at different frequencies to measure impedance.

For performing impedance measurements, one may employ virtually any impedance analyzer known in the art. For example, a Schlumberger Model 1260 Impedance/Gain-Phase Analyzer (Schlumberger Technologies, Farmborough, Hampshire, England) with approximately 6 inch RG174 coaxial cables is employed. In such an apparatus, the resistor/sensor is held in an Al chassis box to shield it from external electronic noise.

In still another embodiment of the present invention, one may vary both the frequency of the electrical current employed and the temperature and measure the electrical impedance, thereby allowing for the detection of the presence of a chemical analyte of interest. Accordingly, the sensor or sensor array is electrically connected to an electrical measuring apparatus and in thermal communication with a temperature control apparatus. For measuring impedance as a function of frequency and temperature, the frequencies employed will generally not be higher than 10 MHZ, preferably not higher than 5 MHZ. Chemical analytes of interest will exhibit unique impedance characteristics at varying alternating current frequencies and varying temperatures, thereby allowing one to detect the presence of any chemical analyte of interest in a sample.

In another procedure, one particular sensor composition can be used in an array and the response properties can be varied by maintaining each sensor at a different temperature from at least one of the other sensors, or by performing the electrical impedance measurement at a different frequency for each sensor, or a combination thereof.

An electronic nose for detecting an analyte in a sample is fabricated by electrically coupling the sensor of an array of differently responding sensors to a measuring device. The device measures changes in signal at each sensor of the array, preferably simultaneously and preferably over time. Where the sensor changes conductivity upon contact with a sample, the signal is an electrical resistance and the measuring device is an electrical measuring apparatus, although it could also be an impedance or other physical property of the material in response to the presence of the analyte in the sample. In one embodiment, the device includes signal processing systems and is used in conjunction with a computer and data structure for comparing a given response profile to a structure-response profile database for qualitative and quantitative analysis. Typically such a nose comprises usually at least ten, often at least 100, and perhaps at least 1000 different sensors though with mass deposition fabrication techniques described herein or otherwise known in the art, arrays of on the order of at least one million sensors are readily produced.

In one mode of operation with an array of sensors, each resistor provides a first electrical resistance between its conductive leads when the resistor is contacted with a first sample comprising a first analyte, and a second electrical resistance between its conductive leads when the resistor is contacted with a second sample comprising a second, different analyte. The sample may be a liquid or gaseous in nature. The first and second sample may reflect samples from two different environments, a change in the concentration of an analyte in a sample at two time points, a sample and a negative control, etc. The sensor array typically will comprise sensors which respond differently to a change in an analyte concentration or identity, e.g., the difference between the first and second electrical resistance of one sensor is different from the difference between the first second electrical resistance of another sensor.

In one embodiment, the temporal response of each sensor (resistance as a function of time) is recorded (see, for example, U.S. patent application Ser. No. 09/568,784, now U.S. Pat. No. 6,455,319, filed May 10, 2000, entitled, "Use of Spatiotemporal Response Behaviour in Sensor Arrays to Detect Analytes in Fluids," the disclosure of which is incorporated herein by reference). The temporal response of each sensor may be normalized to a maximum percent increase and percent decrease in signal which produces a response pattern associated with the exposure of the analyte. By iterative profiling of known analytes, a structure-function database correlating analytes and response profiles is generated. Unknown analytes may then be characterized or identified using response pattern comparison and recognition algorithms. Accordingly, analyte detection systems comprising sensor arrays, an electrical measuring device for detecting resistance across each chemiresistor, a computer, a data structure of sensor array response profiles, and a comparison algorithm are provided. In another embodiment, the electrical measuring device is an integrated circuit comprising neural network-based hardware and a digital-analog converter (DAC) multiplexed to each sensor, or a plurality of DACs, each connected to different sensor(s).

The desired signals if monitored as dc electrical resistance for the various sensor elements in an array can be read merely by imposing a constant current source through the resistors and then monitoring the voltage across each resistor through use of a commercial multiplexable 20 bit analog-to-digital converter. Such signals are readily stored in a computer that contains a resident algorithm for data analysis and archiving. Signals can also be preprocessed either in digital or analog form; the latter might adopt a resistive grid configuration, for example, to achieve local gain control. In addition, long time adaptation electronics can be added or the data can be processed digitally after it is collected from the sensors themselves. This processing could be on the same chip as the sensors but also could reside on a physically separate chip or computer and can be analyzed local or remote to the sensor or sensor array. (See, for example, U.S. patent application Ser. No. 09/596,758, filed Jun. 15, 2000, the disclosure of which is incorporated herein by reference).

Data analysis can be performed using standard chemometric methods such as principal component analysis and SIMCA, which are available in commercial software packages that run on a PC or which are easily transferred into a computer running a resident algorithm or onto a signal analysis chip either integrated onto, or working in conjunction with, the sensor measurement electronics. The Fisher linear discriminant is one preferred algorithm for analysis of the data, as described below. In addition, more sophisticated algorithms and supervised or unsupervised neural network based learning/training methods can be applied as well (Duda, R. O.; Hart, P. E. Pattern Classification and Scene Analysis; John Wiley & Sons: New York, 1973, pp 482).

The signals can also be useful in forming a digitally transmittable representation of an analyte in a fluid (see, for example, U.S. patent Ser. No. 09/596,758, filed Jun. 15, 2000, the disclosure of which is incorporated herein by reference). Such signals could be transmitted over the Internet in encrypted or in publicly available form and analyzed by a central processing unit at a remote site, and/or archived for compilation of a data set that could be mined to determine, for example, changes with respect to historical mean "normal" values of the breathing air in confined spaces, of human breath profiles, and of a variety of other long term monitoring situations where detection of analytes in fluids is an important value-added component of the data.

Twenty to thirty different sensors is sufficient for many analyte classification tasks but larger array sizes can be implemented as well. Temperature and humidity can be controlled. In one embodiment, changes relative to the ambient baseline condition can be analyzed. Because the patterns for a particular type and concentration of odorant are generally independent of such baseline conditions, it is not critical to actively control these variables in some implementations of the technology. Such control could be achieved either in open-loop or closed-loop configurations.

The sensors and sensor arrays disclosed herein could be used with or without preconcentration of the sample or analyte depending on the power levels and other system constraints demanded by the user. Regardless of the sampling mode, the characteristic patterns (both from amplitude and temporal features, depending on the for most robust classification algorithm for the purpose) associated with certain disease states and other volatile analyte signatures can be identified using the sensors disclosed herein. These patterns are then stored in a library, and matched against the signatures emanating from the sample to determine the likelihood of a particular odor falling into the category of concern (disease or nondisease, toxic or nontoxic chemical, good or bad polymer samples, fresh or old fish, fresh or contaminated air, etc.).

Analyte sampling will occur differently in the various application scenarios. For some applications, direct headspace samples can be collected using either single breath and urine samples for the purpose of disease or health state differentiation and classification. In addition, extended breath samples, passed over a Tenax, Carbopack, Poropak, Carbosieve, or other sorbent preconcentrator material, can be obtained when needed to obtain robust intensity signals. The absorbent material of the fluid concentrator can be, but is not limited to, a nanoporous material, a microporous material, a chemically reactive material, a nonporous material and combinations. thereof. In certain instances, the absorbent material can concentrate the analyte by a factor that exceeds a factor of about $10^5$, or by a factor of about $10^2$ to about $10^4$. In another embodiment, removal of background water vapor is conducted in conjunction, such as concomitantly, with the concentration of the sample or analyte. Once the sample or analyte is concentrated, it can be desorbed using a variety of techniques, such as heating, purging, stripping, pressuring or a combination thereof.

Breath samples can be collected through a straw or suitable tube in a subject's mouth that is connected to the sample chamber (or preconcentrator chamber), with the analyte outlet available for capture to enable subsequent GC/MS or other selected laboratory analytical studies of the sample. A subject can be any mammal, but is preferably a human.

In other applications, headspace samples of odorous specimens can be analyzed and/or carrier gases can be used to transmit the analyte of concern to the sensor(s) to produce the desired response. In still other cases, the analyte will be in a liquid phase and the liquid phase will be directly exposed to the sensors; in other cases the analyte will undergo some separation initially and in yet other cases only the headspace of the sample will be exposed to the sensors.

Accordingly, an analyte or sample can be concentrated from an initial sample volume of about 10 liters and then desorbed into a concentrated volume of about 10 milliliters or less, before being presented to a sensor array.

Suitable commercially available adsorbent materials include but are not limited to, Tenax TA, Tenax GR, Carbotrap, Carbopack B and C, Carbotrap C, Carboxen, Carbosieve SIII, Porapak, Spherocarb, and combinations thereof. Preferred adsorbent combinations include, but are not limited to, Tenax GR and Carbopack B; Carbopack B and Carbosieve SIII; and Carbopack C and Carbopack B and Carbosieve SIII or Carboxen 1000. Those skilled in the art will know of other suitable absorbent materials.

In another embodiment, removal of background water vapor is conducted in conjunction, such as concomitantly, with the concentration of the analyte. Once the analyte is concentrated, it can be desorbed using a variety of techniques, such as heating, purging, stripping, pressuring or a combination thereof. In these embodiments, the sample concentrator is wrapped with a wire through which current can be applied to heat and thus, desorb the concentrated analyte. The analyte is thereafter transferred to a sensor array.

In some cases, the array will not yield a distinct signature of each individual analyte in a region, unless one specific type of analyte dominates the chemical composition of a sample. Instead, a pattern that is a composite, with certain characteristic temporal features of the sensor responses that aid in formulating a unique relationship between the detected analyte contents and the resulting array response, will be obtained.

In one embodiment of signal processing, a Fisher linear discriminant searches for the projection vector, w, in the detector space which maximizes the pairwise resolution factor, i.e., rf, for each set of analytes, and reports the value of rf along this optimal linear discriminant vector, The rf value is an inherent property of the data set and does not depend on whether principal component space or original detector space is used to analyze the response data. This resolution factor is basically a multi-dimensional analogue to the separation factors used to quantify the resolving power of a column in gas chromatography, and thus the rf value serves as a quantitative indication of how distinct two patterns are from each other, considering both the signals and the distribution of responses upon exposure to the analytes that comprise the solvent pair of concern. For example, assuming a Gaussian distribution relative to the mean value of the data points that are obtained from the responses of the array to any given analyte, the probabilities of correctly identifying an analyte as a or b from a single presentation when a and b are separated with resolution factors of 1.0, 2.0 or 3.0 are approximately 76%, 92% and 98%, respectively.

To compute the rf, from standard vector analysis, the mean response vector, $x_a$, of an n-sensor array to analyte a is given as the n-dimensional vector containing the mean autoscaled response of each sensors, $A_{aj}$, to the $a^{th}$ analyte as components such that $$x_a = (A_{a1}, A_{a2}, \ldots A_{an}).$$

The average separation, "d", between the two analytes, a and b, in the Euclidean sensor response space is then equal to the magnitude of the difference between $x_a$ and $x_b$. The noise of the sensor responses is also important in quantifying the resolving power of the sensor array. Thus, the standard deviations, $S_{a,d}$ and $S_{b,d}$, obtained from all the individual array responses to each of a and b along the vector d, are used to describe the average separation and ultimately to define the pairwise resolution factor as $$rf = d_w / ((\sigma^2_{a,w} + \sigma^2_{b,w})^{1/2}).$$

Even if the dimensionality of odor space is fairly small, say on the order of $10^1$, there is still interest in being able to model the biological olfactory system in a construction of arrays consisting of large numbers of receptor sites. In practice, correlations between the elements of a sensor array may use a much larger number of sensors to successfully distinguish molecules. Furthermore, performance issues such as response time, signal averaging, or calibration ranges may require multiple sensors based on each material. Analysis of mixtures will add additional degrees of freedom if the components of the mixture are to be individually identified and may use a large number of sensors. Fabrication of a large number of sensors also enables the use of very powerful coherent signal detection algorithms to pull a known, but small amplitude, signal, out of a noisy background.

The following examples are offered by way of illustration and not by way of limitation.

EXAMPLES

Figure 1B:
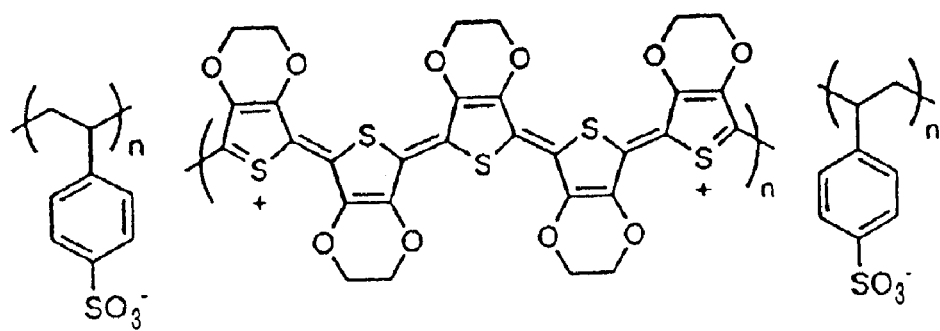
FIG. 1B shows the structure of poly(3,4-ethylene dioxy) thiophene-poly(styrene slfonate), PEDOT-PSS.

Fabrication of a stable and diverse array of chemiresistor-type vapor detectors from soluble, processable, polar conducting organic polymers is provided. The detectors in the sensor array consist of either a blend or composite of commercially available poly(3,4-ethylenedioxy)thiophene (PEDOT-PSS) (FIG. 1) with a number of different insulating polymers. PEDOT-PSS was chosen for several reasons as the conductive polymer used in this study. PEDOT is relatively inexpensive and is sold commercially (Baytron P) as a colloidal suspension in water. The poly(styrene sulphonate), PSS, that is intimately associated through electrostatic attractions with the p-doped poly(3,4-ethylenedioxy)thiophene contributes to the stability of the colloid. PEDOT-PSS films cast from solution have been shown to exhibit superior environmental stability due to both the electron richness concentrated in the polymer backbone and the inertness of the thiophene heterocycle (compared to that of pyrrole) as well as the high conductivity of the material itself. Furthermore, because this material is tractable, fabrication of sensors is simplified compared to alternative techniques for conductive polymer detector fabrication. For example, the fabrication of polypyrrole detectors has entailed the polymerization of the monomer directly onto the detector substrate, making it difficult to insure the same properties of the conductive polymer phase from trial to trail and within the composites in every detector in the array.

The perfomance of an array of PEDOT-PSS sensors was quantified using resolution factors and these values were compared to the performance of an array of carbon black composite sensors that utilized the same insulating matrices. One purpose of the PEDOT-PSS sensor is not to replace carbon black composite sensors but to incorporate PEDOT-PSS composites into a system that provides a wider and more diverse electronic nose array for improved overall vapor detection performance.

Figure 2:
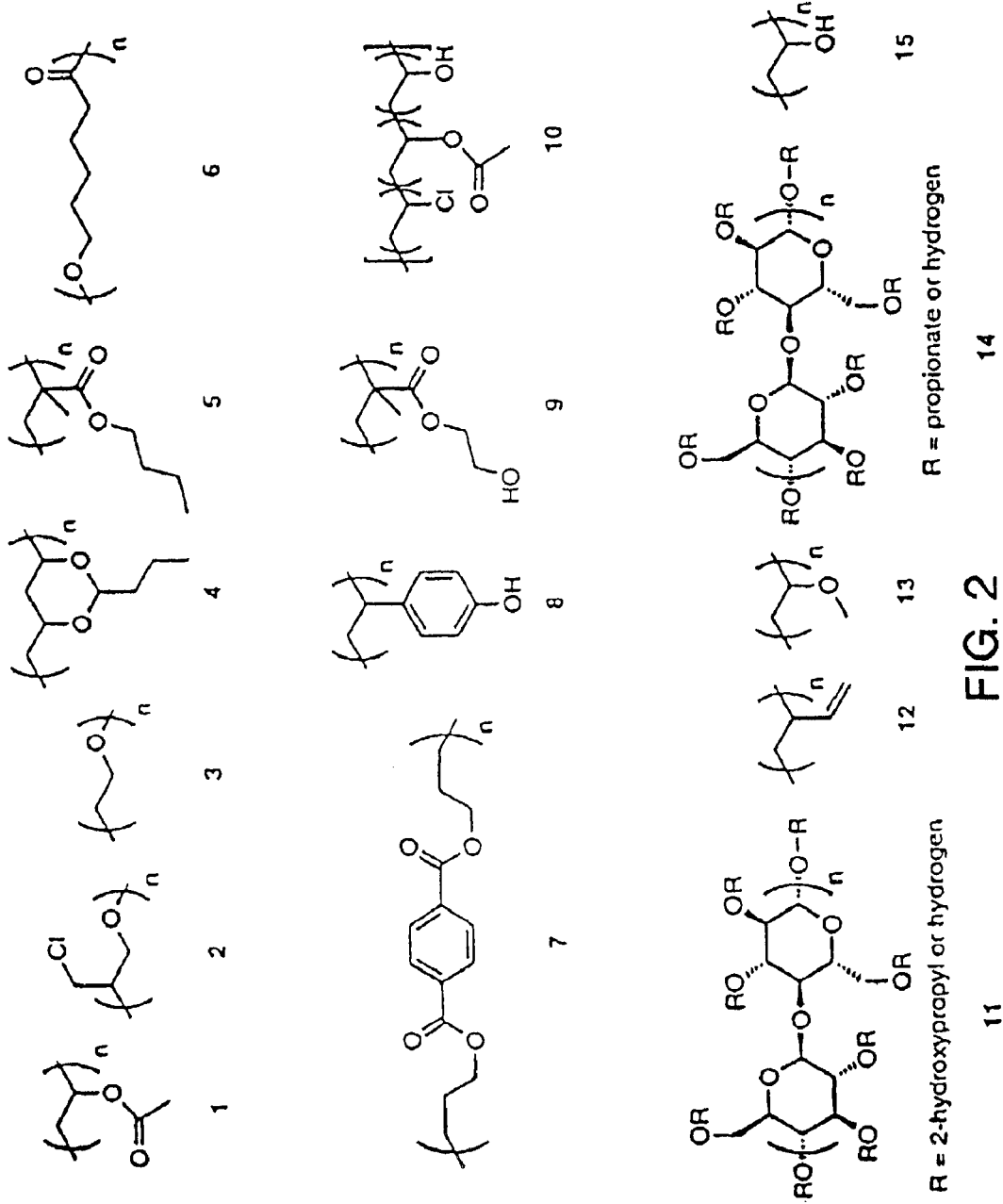
FIG. 2 shows the insulating polymers used in the Examples section which were mixed with PEDOT-PSS or carbon black to yield the detector film.

Materials. The poly(3,4-ethylenedioxy)thiophene-poly(styrene sulfonate) (PEDOT-PSS) (0.5% PEDOT and 0.8% PSS by weight) was supplied as a colloidal suspension in water and was used as received (AG Bayer Inc.). The carbon black used in the composites was Black Pearls 2000 (BP2000) that was generously donated by Cabot Co. (Billerica, Mass.). The insulating polymers used in this study are shown in FIG. 2. Poly(vinyl acetate) ($M_n$ 260,000), poly(epichlorohydrin) (MW 700,000), poly(ethylene oxide) (MW 100,000), poly(vinyl butyral) ($M_n$ 110,000), poly(n-butyl methacrylate) ($M_n$ 180,000), poly(caprolactone) ($M_n$ 30,000), poly(diallylphthalate), poly(2-hydroxyethylmethacrylate) ($M_v$ 300,000), vinyl chloride (91%)/vinyl acetate (6%)/vinyl alcohol (3%) copolymer ($M_n$ 70,000), hydroxypropyl cellulose (MW 60,000), poly(2-butadiene) (MW 100,000), cellulose propionate ($M_n$ 200,000), poly(vinyl alcohol) (16,000), poly(methyl vinyl ether) (50% solids in water, $M_n$ 90,000) and poly(styrene) ($M_n$ 45,000) were used as received from Scientific Polymer Products, Inc. (SP²). Poly(4-vinyl phenol) (MV 8,000) was used as received from Aldrich Chemical Co. The solvents used in this study were methanol, ethanol, ethyl acetate, nitromethane, acetonitrile, acetone, tetrahydrofuran, chloroform, hexane, benzene, methoxybenzene, toluene, chlorobenzene, trifluoromethylbenzene (TFMbenzene), benzaldehyde, and nitrobenzene. These solvents were purchased from Aldrich and were used without further purification.

Apparatus. An automated flow system was used to deliver a diluted stream of solvent vapor to the sensors. The flow system consisted of LabVIEW 5.0.1, a pentium computer, electronically-controlled solenoid valves, three mass flow controllers, and eight bubblers with coarse frits. The background carrier gas was oil-free air obtained from the general compressed air lab source (1.10±0.15 parts per thousand (ppth) of water vapor) controlled via a 50 L min⁻¹ mass flow controller (MKC Inc). The air was filtered before entry into the mass flow controllers but was not dehumidified. In order to obtain the desired concentration of analyte in the gas phase, a stream of carrier gas was passed though a bubbler that contained the desired solvent. The eight bubblers of the system were divided into two banks of four, with each bank being controlled by a separate 500 ml min⁻¹ mass flow controller (MKC Inc.). Saturation of the gas flow through each bubbler was validated both by measurements of the rate of mass loss of the solvent in the bubbler and through calibration of the flow reaching the detector chamber using a flame ionization detector (Model 300 HFID, California Analytical Instruments, Inc.). The flame ionization detector was calibrated with toluene standards (50, 100, 200, 1000 ppm) that were purchased from Matheson Inc. The calibrations indicated that the flow system had an ~5% random error in the delivery of a preset concentration of toluene between various trials, and no attempts were made to correct for this equipment-derived error in the reported detector response data. The temperature during data collection was 21.5±0.5° C. but no active temperature control was maintained over the detectors.

Detector Fabrication. Sensor substrates were fabricated by evaporating 200 nm of chrome and then 800 nm of gold onto glass microscope slides using 2.5 mm wide drafting tape as a mask. After evaporation the mask was removed and the slides were baked at 300° C. for 12 hours. The glass slides were then cut to yield the detector substrates.

The concentrations of the insulating polymer in the respective solvent ranged from 1 mg ml⁻¹ to 10 mg ml⁻¹. Solvents were either tetrahydrofuran (polymers 1, 6, 8, 10 and 12), acetone (polymers 2, 4, 5, 7, and 14), methanol (polymer 9) or water (polymers 3, 11, 13, and 15). Five grams of the as-received PEDOT-PSS solution were added to each of the polymer solutions (typically 10 ml in volume; exact details are contained in Table 5). The stock solution of PEDOT-PSS was diluted in order to obtain the blends for polymer 9 having <40% PEDOT-PSS. In these dilutions, the PEDOT-PSS stock solution was diluted to obtain the desired weight percentage of PEDOT relative to the insulating polymers, but the volume of PEDOT solution was maintained at 5 ml. The PEDOT-PSS solution was added dropwise to the solution containing the insulating polymer. All aqueous solutions were stable, whereas aqueous solutions of polymer and organic solvents resulted in precipitation of polymer after about 2 weeks of storage for polymers 1, 2, 4, 6, 10, and 12.

TABLE 5

| Composite | Solvent* | Concentration (mg/ml) |
|---|---|---|
| 1 | tetrahydrofuran | 10 |
| 2 | acetone | 10 |
| 3 | water | 10 |
| 4 | acetone | 10 |
| 5 | acetone | 10 |
| 6 | tetrahydrofuran | 10 |
| 7 | acetone | 5 |
| 8 | tetrahydrofuran | 10 |
| 9 | methanol | 10 |
| 10 | tetrahydrofuran | 5 |
| 11 | water | 10 |
| 12 | tetrahydrofuran | 5 |
| 13 | water | 1 |

TABLE 5-continued

| Composite | Solvent* | Concentration (mg/ml) |
|---|---|---|
| 14 | acetone | 10 |
| 15 | water | 10 |

*Solvent used to dissolve the insulating polymer. IN order to obtain the film castin solutino the colloidal suspensin of PEDOT-PSS was slowly added to the solution continaing the insulating polymer Thin films (between 90 and 900 nm thick, as measured by profilometry) were obtained by spin coating (Headway Research Inc.) the solution of PEDOT-PSS and insulating polymer onto the substrate. The solution was applied dropwise via a pasteur pippette while the substrate was spinning at 1000 rpm. The film thickness was increased by continuing to add drops of the polymer solution until the dc resistance of the resulting film was 100–200 k$\Omega$. After fabrication, all of the detectors were placed in a stream of dry air for 40 hours to allow for the off-gassing of solvent vapor. Upon inspection under a Leica StereoZoom 6 optical microscope (30×), PEDOT-PSS loaded films obtained using polymers 2, 3, 5, 7, 9, 11, 13, 14, and 15 appeared to be homogenous, whereas with polymers 1, 4, 6, 8, 10, and 12 the films were heterogenous in that PEDOT-PSS clumps and strands were noticeable. The polymers listed above all made detectors that yielded good electrical responses to the various analytes of interest.

Carbon black composite detectors were prepared by first dissolving approximately 200 mg of insulating polymer in the appropriate solvent (the same solvents were used as those described above for PEDOT-PSS composite preparation) and then adding 50 mg of carbon black such that the overall composition of the solution was 80% insulating polymer:20% carbon black by weight. These solutions were sonicated for approximately 20 minutes and detector films were then spin cast by covering the detector substrate with solution. As for the PEDOT films, solution was deposited until the films had resistance values of 100–200 k$\Omega$. The resulting film thicknesses were in typically in the range of 100–500 nm. Detectors were then placed in a stream of dry air for 40 hours.

Conductivity and Mass Uptake Measurements. Conductivity measurements were performed using the 4 point colinear array technique. Current was supplied to the outer leads using a potentiostat (Pine Instrument Co.) and was monitored using a multimeter (Fluke 87). A multimeter was used to measure the voltage drop across the inner leads. To ensure that the materials followed ohmic behavior, the voltage drops were measured for at least 4 different applied currents for each film. The substrate used for the measurement consisted of four evaporated gold leads deposited onto a glass backing. The distance between each set of gold leads was 0.212 cm. All films were prepared by the spin coating technique described above.

For determining the resistance response to the presence of solvent vapors, the resistive film detectors were housed in an aluminum chamber, and two electrical leads were connected via alligator clips to each detector. The leads were multiplexed through a Keithley model 7001 channel switcher to a Keithley model 2002 multimeter that measured the resistance of each detector approximately once every three seconds.

QCM crystals (10 MHz, blank diameter=13.7 mm) with a custom electrode pattern were obtained from International Crystal Manufacturing (ICM) in Oklahoma City, Okla. The resonant frequency of the QCM was obtained using a HP 53181A frequency counter (Palo Alto, Calif.). Shielded cables were used between the crystal, the oscillator circuit, and the frequency counter. The standard oscillation electrodes were configured at 90° angles to make room for two other tabs that would serve as electrodes for resistance measurements of the carbon black-polymer composite and PEDOT PSS-polymer composite films. The crystals were polished to a surface roughness of less than 5 $\mu$m, which produced a mirror-like finish on the gold electrodes.

Flow System Measurements. Flow system experiments were carried out using the apparatus described above. All sensors were purged with carrier gas for two hours before each separate flow system experiment. Prior to data collection, all of the detectors were subjected to ten exposures to each of the sixteen different solvents used in this study, with each analyte at 5% of its vapor pressure at room temperature.

The data were obtained during seven separate flow system experiments. Five of the flow system experiments consisted of eighty exposures to eight separate analytes (10 exposures to each analyte) at a constant activity (5% of the analyte's vapor pressure). The concentrations of analyte in this run were (in units of parts per thousand ppth)): methanol (6.63), ethanol (3.21), ethyl acetate (4.87), nitromethane (1.90), acetonitrile (4.90), acetone (12.9), tetrahydrofuran (9.02), chloroform (10.7), hexane (9.74), benzene (5.21), methoxybenzene (0.181), toluene (1.55), chlorobenzene (0.641), trifluoromethylbenzene (0.217), benzaldehyde (0.059), and nitrobenzene (0.011). Each exposure consisted of a three-step process that began with 240 s of air flow over the detector followed by a 300 s period in which the analyte was present in the vapor stream. Finally, the detectors were exposed to background air for another 240 s. All exposures for each separate flow system experiment were fully randomized with respect to analyte identity. Two copies of each detector were used, and the responses for both detectors of a given composition were combined with the response to multiple exposures to a given analyte to produce a reported response quantity for that analyte/detector combination.

The flow system experiment for the study of response vs analyte concentration was similar to that described above except that two solvents (methanol and nitromethane) were used at 5, 3, 1, and 0.5% of each analyte's vapor pressure. This is equivalent to concentrations of 6.63, 3.98, 1.32, 0.66 ppth for methanol and 1.90, 1.14, 0.380, 0.190 ppth for nitromethane. Exposures for this experiment were not randomized and followed the order of being exposed first to methanol, from lowest to highest concentration (a total of 40 exposures, 10 exposures at each of the four different concentrations), followed by the exposures to nitromethane, again from the lowest to highest concentration (a total of 40 exposures, 10 exposures at each of the four different concentrations). The calculated responses reported for each concentration were an average of 20 data points, 10 exposures for each of the pair of nominally identical detectors of a given composition.

The experiment using different loading levels of PEDOT-PSS with polymer 9 was performed using four copies of each detector type. Five exposures were performed for each of the two analytes (methanol and acetonitrile) so that the reported responses are an average of twenty data points. The exposures to the analytes were not randomized but instead five exposures to methanol at 3% (3.98 ppth) of its vapor pressure were performed, followed by five exposures to acetonitrile at 3% (2.98 ppth) of its vapor pressure.

Figure 3:
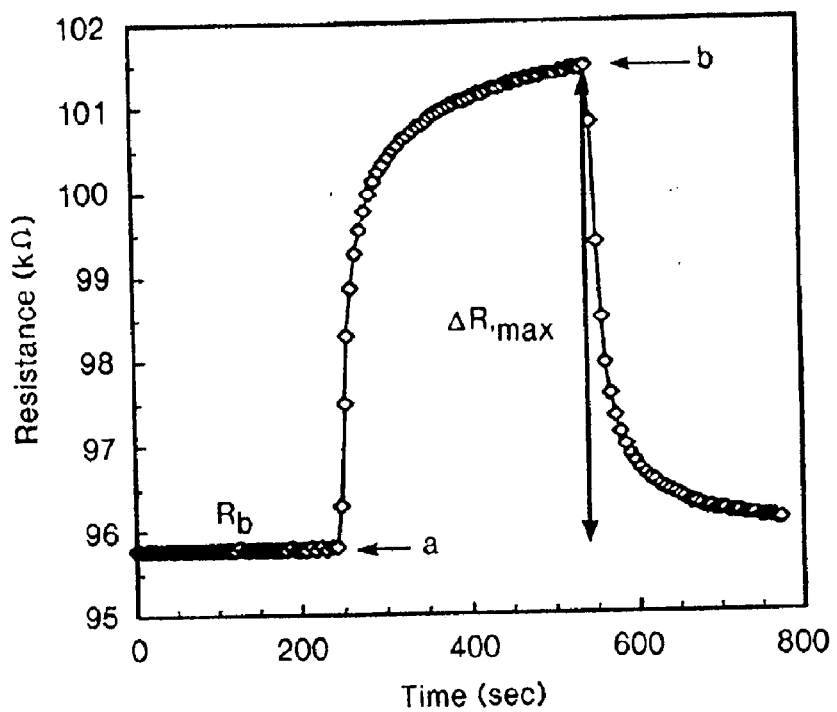
FIG. 3 is a graph depicting the exposure of a PEDOT-PSS/7 detector to methanol at 5% of its saturated vapor pressure. At time, a, the methanol vapor was introduced into the carrier gas which was directed over the detectors. At time, b, the methanol vapor was removed from the carrier gas. The general shape of the response in this figure is representative of exposures analyzed as described below.

Data Processing. All data were first corrected to remove any drift in the baseline resistance. This drift correction was also applied to the resistance data obtained for the detector during exposure to that particular analyte. Then the maximum relative differential resistance change, $\Delta R_{ij,max}/R_b$, was calculated, where $\Delta R_{ij,max}$ is the maximum differential resistance change, taken as the average of five data points about the maximum measured differential resistance of the $j^{th}$ detector during the $i^{th}$ exposure, and $R_b$ is the drift-corrected baseline resistance of the detector prior to the exposure. A sample response for a PEDOT-PSS/7 composite detector is shown in FIG. 3.

Quantification of Detector Array Performance. Statistical methods based on cluster analysis using the Fisher linear discriminant methodology were used to analyze the detector array data. A resolution factor for any solvent pair can be obtained along any vector, $\vec{w}$, from the vector projection onto $\vec{w}$ of the distance between the cluster centroids, $d_{\vec{w}}$, divided by the sum of the projected standard deviations, $\sigma_{a,\vec{w}}$ and $\sigma_{b,\vec{w}}$, for data arising from repeated exposures for two different analytes, a and b. The resulting numerical resolution factor along $\vec{w}$ is defined as:

$$rf = d_{\vec{w}} / \sqrt{\sigma_{a,\vec{w}}^2 + \sigma_{b,\vec{w}}^2}$$

The Fisher linear discriminant operates by searching for the vector, $\vec{w}$, such that the rf value is maximized along this optimal discriminant vector. Assuming a Gaussian distribution relative to the mean value of the data points in a given cluster, the probabilities of correctly identifying an analyte as a or b are approximately 72, 92 and 98% from a single presentation when analytes a and b are separated with resolution factors of 1.0, 2.0, or 3.0, respectively. Data extracted from multiple exposures of an analyte only estimate the statistical distributions of the clustered data, which may lead to an overestimation of rf. Overestimations are typically less than 30% for an array consisting of 14 detectors and the given number of solvent exposures, with the overestimations dropping to less than 3% in cases involving a single-detector. Especially large rf values should be treated with caution as they could be overestimated by larger amounts.

For the resolution factors calculated for both the PEDOT-PSS detector array and the carbon black composite array, the best detector of the two copies that was prepared with each of the first nine insulating polymers, as determined by the lowest standard deviation in the response across the ten exposures to a given analyte, was used. Comparisons of resolution factors were made between a nine detector array of PEDOT-PSS composites composed of insulating polymers 1 through 9 and a nine detector array of carbon black composite detectors. The same nine insulating polymers were used in both array types.

Conductivity, Short Term Drift, Long Term Drift, and dc Noise Levels of the PEDOT-PSS Composite Films. Table 6 lists the dc conductivities measured for several poly(3,4-ethylenedioxy)thiophene-poly(styrene sulfonate), PEDOT-PSS, films loaded with 40% by weight PEDOT-PSS. Films exhibiting the highest conductivities were those prepared using poly(vinyl acetate) (1), poly(n-butylmethacrylate) (5) and poly(caprolactone) (6). These films exhibited conductivities ranging from approximately 100 to 360 S cm$^{-1}$, whereas PEDOT-PSS itself had a conductivity of 30 S cm$^{-1}$. The lowest conductivities were obtained for PEDOT-PSS/15, PEDOT-PSS/9 and PEDOT-PSS/3.

TABLE 6

| PEDOT-PSS Film | R (kΩ)[a] | R (kΩ)[b] | σ (S cm$^{-1}$) | σ (S cm$^{-1}$)[b] |
|---|---|---|---|---|
| 1 | 4.748 (91) | 63.0 (32) | 121 | 9.10 |
| 1 | 5.413 (80) | 53.6 (14) | 360 | 36.3 |
| 2 | 38.820 (50) | 924 (5) | 18.9 | 0.79 |
| 2 | 44.440 (59) | 648 (30) | 29.4 | 2.02 |
| 3 | 231.9 (38) | 4333 | 19.5 | 1.04 |
| 3 | 156.5 (14) | 2845 | 10.9 | 0.63 |
| 4 | 14.02 (18) | 86.9 (57) | 66.3 | 10.7 |
| 4 | 8.636 (141) | 59.7 (52) | 63.6 | 9.21 |
| 5 | 13.01 (11) | 268 (60) | 142 | 6.92 |
| 5 | 10.89 (14) | 80.1 (90) | 198 | 27.1 |
| 6 | 6.827 (118) | 36.6 (52) | 261 | 48.8 |
| 6 | 8.704 (115) | 45.8 (41) | 163 | 29.6 |
| 7 | 22.12 (43) | 204 (12) | 53.0 | 5.71 |
| 7 | 31.25 (29) | 288 (57) | 92.9 | 10.1 |
| 8 | 7.118 (92) | 31.5 (6) | 152 | 12.8 |
| 8 | 7.621 (126) | 27.3 (28) | 38.4 | 10.9 |
| 9 | 212.6 (18) | 1205 (60) | 11.5 | 2.09 |
| 9 | 297.8 (50) | 1158 (50) | 11.5 | 2.95 |
| 15 | 4739 (183) | 3320 (650) | 0.32 | 0.48 |
| 15 | 5261 (247) | 3290 | 0.22 | 0.34 |
| 15[c] | 3524 (29) | 2580 | 0.32 | 0.44 |
| 15[c] | 6055 (671) | 2850 | 0.43 | 0.90 |
| P[d] | 42.52 (39) | 420 (16) | 35.1 | 3.55 |
| P[d] | 38.43 (72) | 382 (15) | 23.9 | 2.40 |

[a]Average resistance obtained from a minimum of four current settings. Standard deviations are given in apprentices as the last digits of the average.
[b]Average resistance values and conductivities measured after 16 months of storage in the dark.
[c]Composition of poly(vinyl alcohol) to PEDOT-PSS is 80 to 20 (wt:wt).
[d]Pure PEDOT-PSS Table 6 also lists the conductivities for the same PEDOT-PSS films after 16 months of storage under atmospheric conditions in the dark. Over this time period, all samples exhibited a decline of approximately one order of magnitude in their conductivities, with the exception of the PEDOT-PSS/15 samples.

In flow system experiments, the mean short term drift of the baseline resistance for the entire set of detectors in a PEDOT-PSS detector array was less than 38±30 Ω/min, while the detector with the largest drift in the array showed a short term baseline resistance change of 180 Ω/min. For comparison, the average baseline drift for the array of carbon black/insulating polymer composite detectors was 105 Ω/min. The baseline drift was negative for all of the PEDOT-PSS and carbon black composite detectors. The average dc noise level (in an ~1 Hz bandwidth) for all detectors across the PEDOT-PSS array was about 1 part in 10,000, which is comparable to the noise levels obtained for the detectors in the carbon black composite array under similar conditions.

Array-Based Vapor Sensing Using PEDOT-PSS Composite Sensors.

Figure 4A:
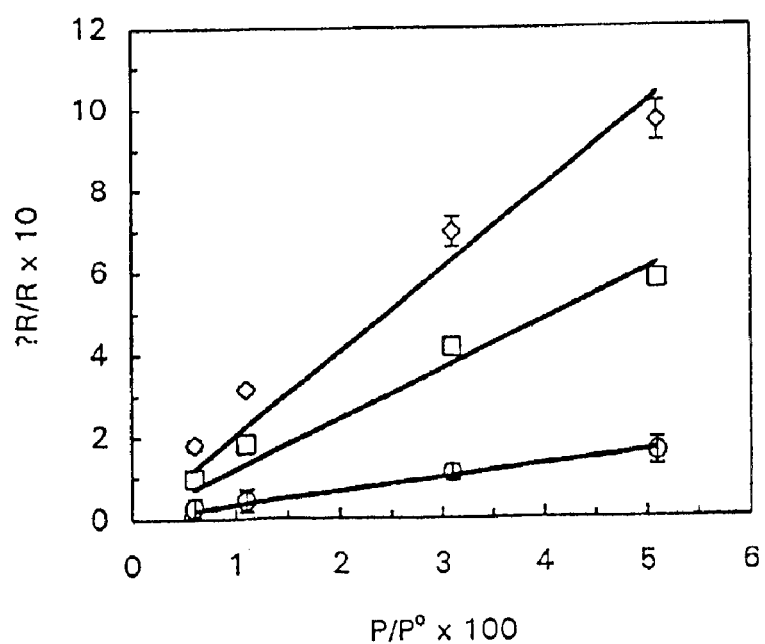
FIG. 4A is a plot of the relative differential resistance response, $\Delta R_{max}/R_b$, for 3 different PEDOT-PSS composite detectors as a function of the concentration of methanol in the gas phase. The methanol (having a vapor pressure $P°$) was maintained at a partial pressure P in a stream of air flowing over the detectos. Squares=PEDOT-PSS/1, Diamonds=PEDOT-PSS/2, and Circles—PEDOT-PSS/3.

FIG. 4A displays a plot of the relative differential resistance response versus analyte concentration for three different PEDOT-PSS detectors exposed to methanol vapor. The fitting statistics of these data are summarized in Table 7. The pristine PEDOT-PSS and PEDOT-PSS/9 detectors were the most sensitive to methanol vapor, displaying a sensitivity value of $(\Delta R_{max}/R_b)/(P/P°)$ (where P is the partial pressure of the analyte in the carrier gas and P° is the vapor pressure of the analyte) of 2.4 and 1.9, respectively. The most sensitive detectors to nitromethane were PEDOT-PSS/3 and PEDOT-PSS/7, which had $(\Delta R_{max}/R_b)/(P/P°)$ values of 0.35 and 0.31, respectively.

Figure 4B:
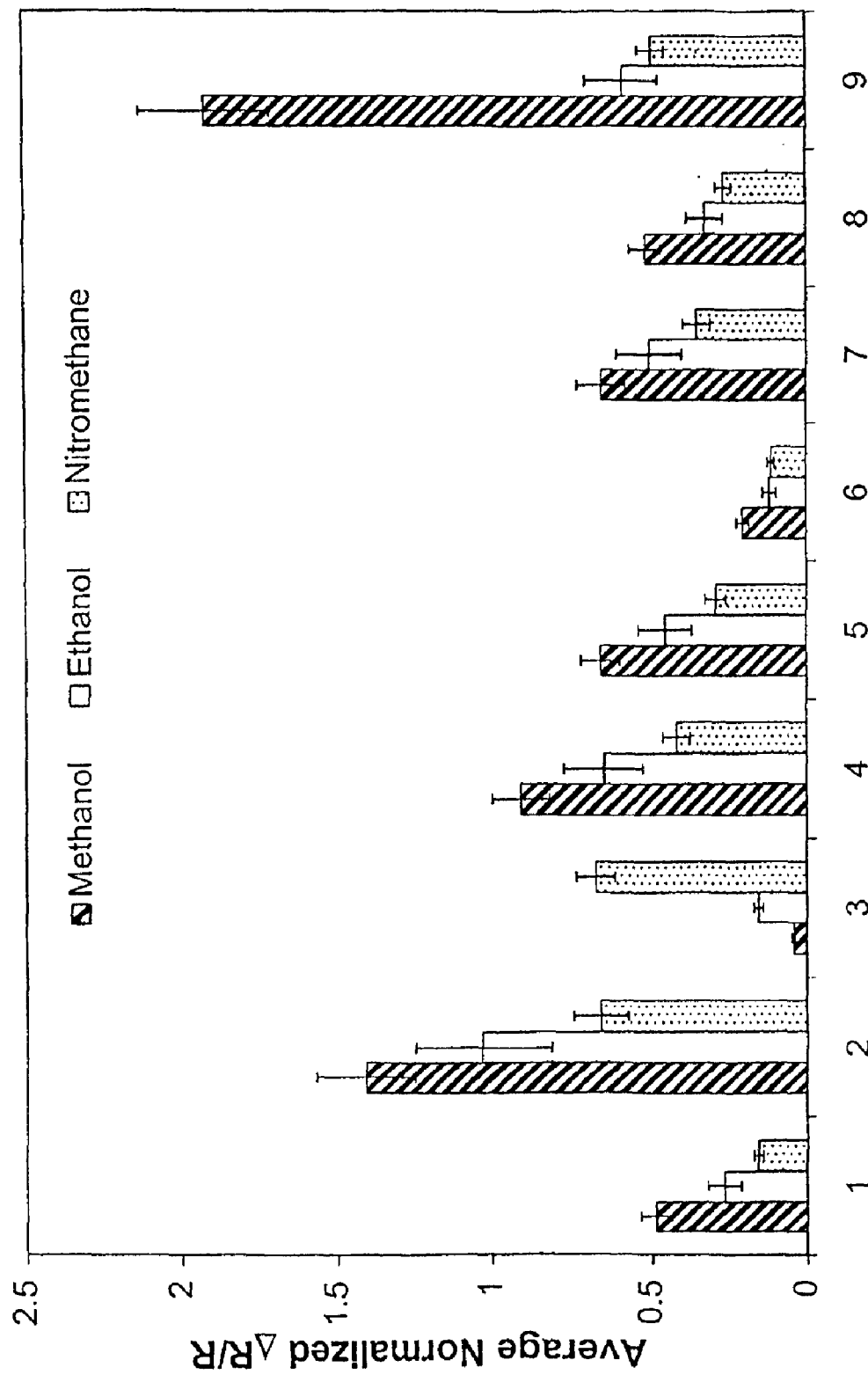
FIG. 4B is a histogram obtained for a PEDOT-PSS detector array upon multiple exposures to ethanol, methanol and nitromethane to 5% of their saturated vapor pressure. Error bars are reported as one standard deviation unit.

FIG. 4B presents the ΔR/R fingerprints obtained for three different analyte vapors exposed to an array comprised of nine compositionally different PEDOT-PSS composite detectors. The data displayed in the figure are the $\Delta R_{max}/R_b$ response values that have been normalized with respect to the maximum $\Delta R_{max}/R_b$ response value obtained across all detectors for a given solvent vapor exposure. The purpose of normalization was to remove the concentration dependence of the data and to isolate the differences in the patterns of array response observed for each of the three solvents. Each separate analyte clearly produced a unique response pattern on this array of detectors.

FIG. 5 is a table that lists the relative differential resistance responses for all PEDOT-PSS detectors during exposure to each of sixteen different analytes. The detectors were especially sensitive to the more polar analytes such as methanol, ethanol, nitromethane, acetonitrile, and acetone. The relative response of the different PEDOT-PSS composite detectors to the various analytes was primarily dictated by the response properties of the PEDOT-PSS itself. The composites did however affect this basic response behavior somewhat, such that some PEDOT-PSS composite detectors showed lower sensitivities to a given analyte than the pristine PEDOT detectors, while others exhibited higher sensitivites. For example, PEDOT-PSS/11 showed a significantly enhanced response to all of the analytes in comparison to the pristine PEDOT-PSS detector.

The differences in response properties between different PEDOT-PSS composites were sufficient to provide robust analyte vapor classification information from the array response data. FIG. 6 is a table that lists the resolution factors obtained for an array of nine PEDOT-PSS composites consisting of the first nine insulating polymers listed in FIG. 2. In this analysis, the data were not normalized but all analytes were evaluated at a fixed fraction of their vapor pressure. The best resolution factor obtained was 360, for the pairwise discrimination between methanol and hexane. In general the best resolution factors were observed for the discrimination of polar analyte pairs and for polar/nonpolar analyte pairs, while low resolution factors were encountered for the discrimination of pairs of nonpolar of compounds. The polar group of analytes, taken as those having a dielectric constant, $\epsilon$, >17, consisted of (dielectric constants in parentheses): nitromethane (37.3), acetonitrile (36.6), nitrobenzene (35.6), methanol (33.0), ethanol (25.3), acetone (21.0), and benzaldehyde (17.9). The nonpolar analytes, taken as those having $\epsilon<10$, consisted of: trifluoromethylbenzene (9.2), tetrahydrofuran (7.5), ethyl acetate (6.1), chlorobenzene (5.7), chloroform (4.8), methoxybenzene (4.3), toluene (2.4), benzene (2.3), and hexane (1.9). The average resolution factor obtained for the discrimination between pairs of polar analytes was 34, with a minimum of 3.4 obtained for the pairwise discrimination of benzaldehyde/nitrobenzene. The average resolution factor for distinguishing polar from nonpolar analytes was calculated to be 47, with a minimum rf of 1.7 obtained for the pairwise discrimination of benzaldehyde/benzene. Discrimination of nonpolar/nonpolar compounds displayed an average resolution factor of 5.0, with a minimum of 1.6 for the discrimination between bezene and trifluoromethylbenzene.

When normalized responses were used, the average rf across all pairwise discriminations was 11, with a minimum of 1.6 (compared to 33 and 1.6 for the untreated responses used for the rf calculations in FIG. 7). The same trends in the pairwise discriminations for the rf calculations using the untreated data were observed in the rf values obtained using the normalized responses.

Array-Based Vapor Sensing Using Carbon Black Composite Detectors.

Carbon black composite detectors consisting of the first nine polymers listed in FIG. 2 were studied to compare their sensitivities and pairwise analyte-resolving properties to those of a PEDOT-PSS detector array formed from the same nine insulating polymers. FIG. 7 is a table that lists the relative differential resistance responses for these carbon black composite detectors upon exposure to each of sixteen different analytes. As for the PEDOT-PSS array, these experiments were performed at a constant activity (P/P°= 0.05) of all analytes. The response trends are in accord with data reported earlier for carbon black composite detectors in that the composites most responsive to polar analytes contained the most polar polymers, whereas the detectors most sensitive to the nonpolar analytes contained the most nonpolar polymers in the array. For example, the largest response to methanol was obtained for the carbon black composite detectors formed from polymers 8 and 9, both of which are good hydrogen bond donors and acceptors. The most sensitive detector to benzene was CB/5. The unsaturated backbone of 5, in addition to a butyl side chain, contribute to this detector's effectiveness in responding to this class of analytes.

Figure 8:
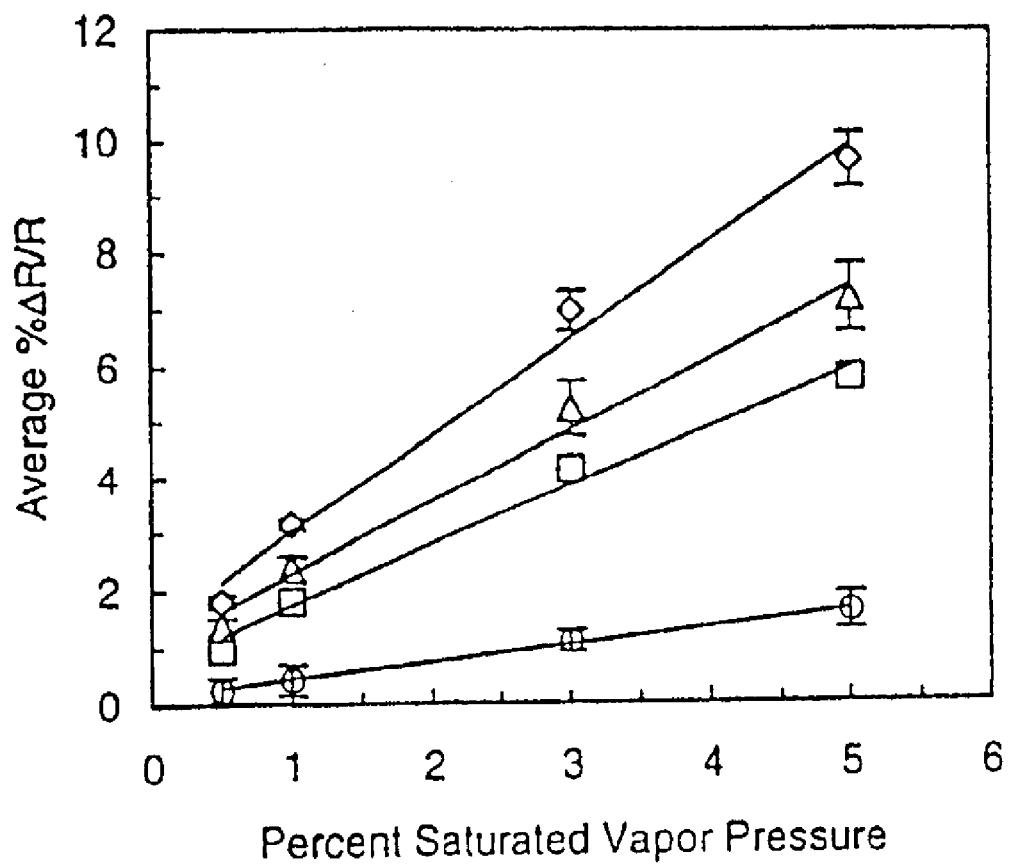
FIG. 8 is a linearity study performed on 4 different PEDOT-PSS composite detectors.

FIG. 8 shows a plot of the average differential resistance response versus the percent saturated vapor pressure for methanol for four different PEDOT-PSS detectors. a total of four different activities were measure or both methanol and nitromethane and both the slopes and their respective $R^2$ values obtained from this data are listed in Table 7. It should be noted that of the detectors tested in the linearity studies, the most sensitive detects to methanol were the pristine PEDOT-PSS and PEDOT-PSS/9 giving slopes of 2.37 and 1.93/% of its saturated vapor pressure (1.32 ppth); whereas the most sensitive to nitromethane were PEDOT-PSS/3 and PEDOT-PSS/7 which had slopes of 0.354 and 0.307/% of its saturated vapor (0.380 ppth).

TABLE 7

PEDOT-PSS composite detector sensitivities to Methanol and nitromethane

| Detector | Slope (Methanol) | R2 | Slope (Nitromethane) | R2 |
| --- | --- | --- | --- | --- |
| PEDOT-PSS | 2.373 | 0.990 | 0.281 | 0.991 |
| 1 | 1.059 | 0.998 | 0.213 | 0.990 |
| 2 | 1.732 | 0.988 | 0.263 | 0.991 |
| 3 | 0.282 | 0.991 | 0.354 | 0.992 |
| 4 | 1.476 | 0.987 | 0.299 | 0.991 |
| 5 | 1.233 | 0.987 | 0.261 | 0.991 |
| 6 | 0.805 | 0.989 | 0.177 | 0.995 |
| 7 | 1.285 | 0.987 | 0.307 | 0.989 |
| 8 | 1.012 | 0.980 | 0.259 | 0.998 |
| 9 | 1.925 | 0.932 | 0.259 | 0.995 |

The resolution factors for a 9-detector carbon black composite array consisting of the first nine polymers in FIG. 2 were calculated using the relative differential resistance values of FIG. 7. The average of all of the resolution factors listed in the table is 30, with a minimum rf of 4.0 obtained for the pairwise discrimination of toluene and hexane (FIG. 13). The average rf for discrimination between pairs of polar solvents is 30, with the worst polar solvent pair being nitrobenzene and benzaldehyde; whereas, the average rf for discrimination of polar/nonpolar analyte pairs was 37. The average rf for the pairs of nonpolar analytes was calculated to be 16. The resolution factors for the carbon black detector array were also calculated using normalized responses.

Again the same trends in rf factors were observed. The average resolution factor obtained across all pairs using the normalized data was 35, slightly higher than that obtained with the unnormalized responses.

Resistance and Quartz Crystal Microbalance Measurements. To assess whether the enhanced sensitivity to polar analytes was predominantly due to an increased mass uptake of the PEDOT-containing films or to an increased $\Delta R/R$ sensitivity of the PEDOT-containing materials, mass uptake measurements were performed simultaneously with resistance change measurements. As displayed in FIG. 9, data were collected for carbon black composites and PEDOT composites using two representative polymers, poly(vinyl butyral) and poly(2-hydroxyethylmethacrylate), during exposures to acetone, methanol, THF, and toluene.

Significant differences were observed between the analyte sorption properties and the relative differential resistance responses of the PEDOT-containing detectors relative to the properties of the carbon black composites. For example, methanol partitioned slightly more favorably into a PEDOT/poly(vinyl butyral) detector than into a carbon black/poly(vinyl butyral) detector, but toluene partitioned more strongly into the carbon black composite than the PEDOT-containing film. Similar behavior was observed for poly(2-hydroxyethylmethacrylate) composites. These data suggest an increased polarity of the PEDOT films relative to the carbon black composites, so that PEDOT films produce increased partition coefficients for polar analytes but decreased partition coefficients for nonpolar analytes.

This increased analyte sorption process was not, however, sufficient to explain the improved $\Delta R/R$ response of the PEDOT-containing films to the polar analytes. In fact, as shown in FIG. 9, the relative differential resistance response with respect to $\Delta f/f$, which is proportional to the relative mass change of the detector film, is much enhanced for the polar compounds, such as methanol, on the PEDOT films relative to the analogous carbon black composites. This indicates that, for polar analytes, the PEDOT-containing films possess an inherent amplification of the sorption-induced signal transduction relative to carbon black composites.

Figure 10:
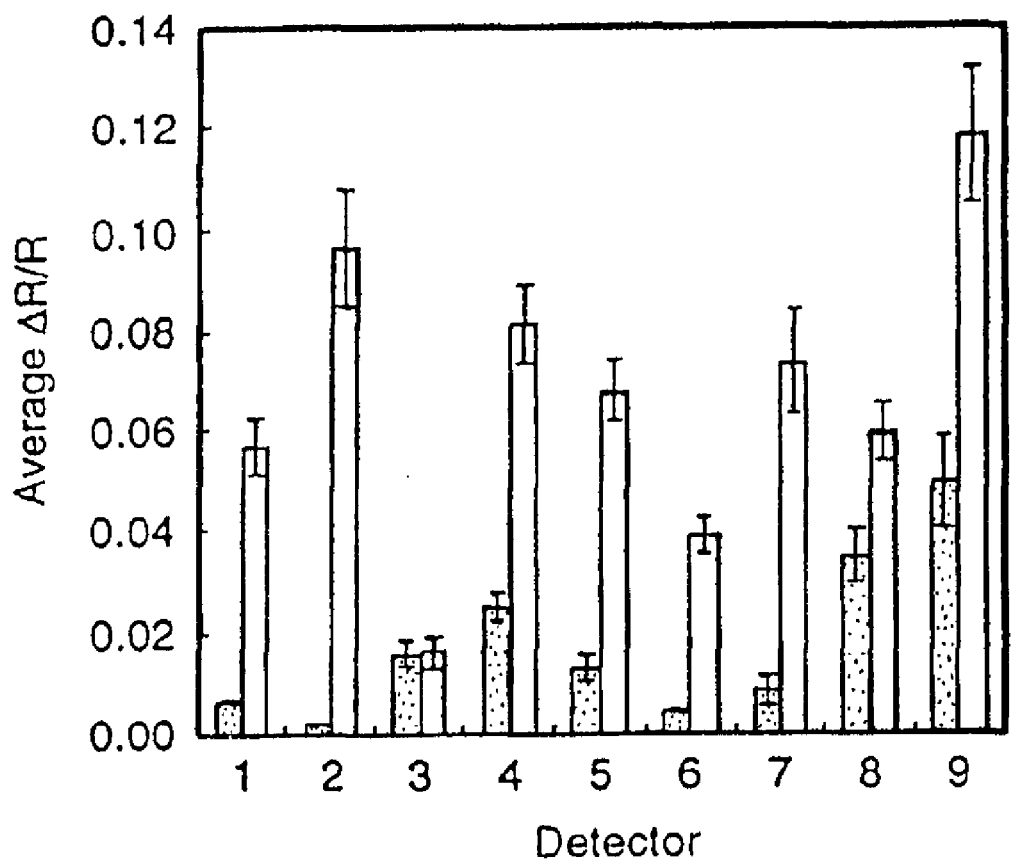
FIG. 10 shows a comparison between the carbon black (shaded) and the PEDOT-PSS (Not shaded) sensor array. The analyte is methanol at 5% of its vapor pressure.
Figure 11:
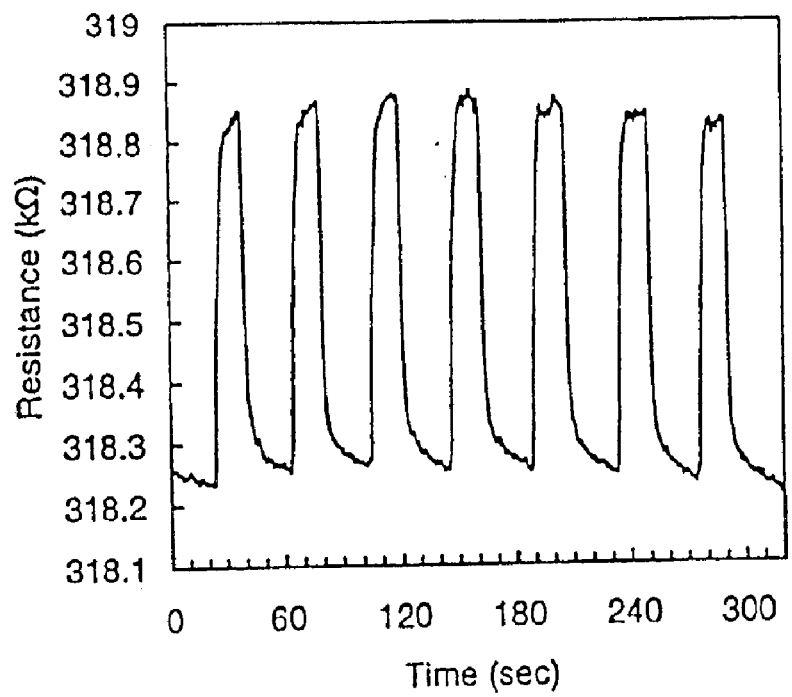
FIG. 11 shows seven consecutive exposures of a PEDOT-PSS/poly(styrene) bilayer detector to cyclohexane at 2% of its saturated vapor pressure.
Figure 12:
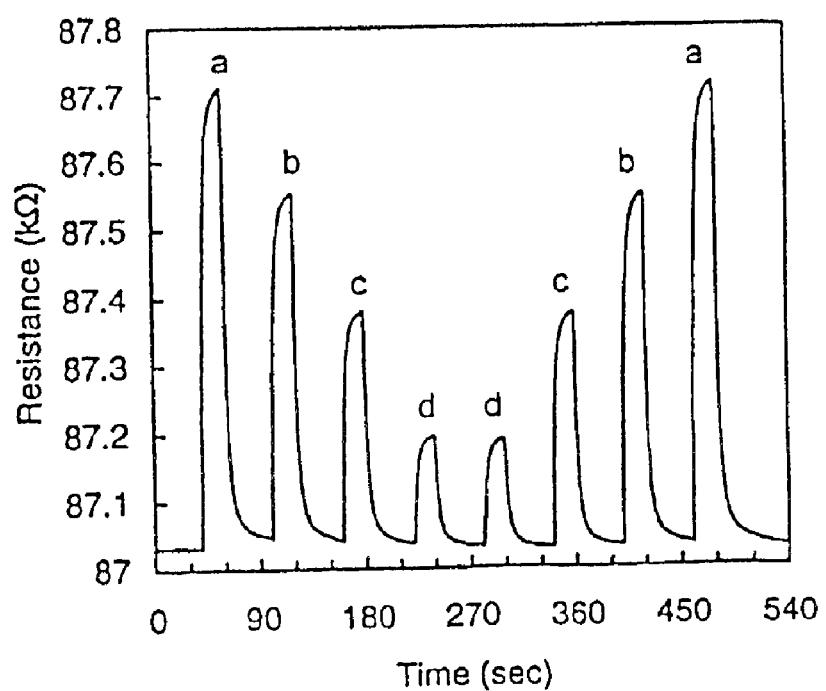
FIG. 12 shows eight consecutive exposures of a PEDOT-PSS/poly(caprolactone) to acetone at four different activities (2, 1.5, 1, and 0.5%), 2 exposures at each concentration.

In general, the PEDOT-PSS detectors were more sensitive than the respective carbon black detectors to polar compounds. FIG. 10 shows the relative differential resistance responses obtained upon exposure to methanol at 5% of its vapor pressure to both a 9-detector PEDOT-PSS and a 9-detector carbon black composite array. All responses for the PEDOT-PSS array were larger than those for the carbon black detectors made using the same insulating polymer. The least responsive of the conductive polymer detectors, PEDOT-PSS/6 was only slightly less responsive than the most responsive carbon black detector towards this particular analyte vapor.

The differential resistance vs. analyte sorption measurements show that, in raw fact, the enhanced signal displayed by PEDOT films when exposed to polar analytes arises predominantly from an increased sensitivity in the conduction mechanism of the PEDOT to the presence of polar analytes relative to that displayed by carbon black composites. Accordingly, better signal/noise performance for polar analytes can be obtained using PEDOT-containing detectors than using the test set of carbon black composites alone for vapor detection tasks.

Using the resolution factors calculated using the Fisher linear discriminant, the PEDOT-PSS detector array was shown to outperform, on average, the carbon black sensor array in the pairwise discrimination of polar analytes and the pairwise discrimination of polar/nonpolar analyte pairs, whereas the carbon black detector array outperformed the PEDOT-PSS array in distinguishing between nonpolar analyte pairs. This behavior is a direct consequence of the increased sensitivity to polar compounds that is obtained by use of the PEDOT materials as opposed to the carbon black-filled composites.

Combinations of PEDOT-PSS detectors and carbon black detectors were also evaluated for their performance in vapor detection tasks. To avoid bias in the selection of an array of detectors, nine PEDOT-containing detectors and nine carbon black composite detectors were selected, each containing one member of polymers 1–9 in FIG. 2. Nine-member arrays were then randomly selected from these 18 detectors. The rf values for pairwise resolution of the test solvents were then tabulated and the performance of these arrays in resolving solvents pairwise were compared to the performance of 9-member arrays containing only the PEDOT composite or the carbon black composite detectors.

As displayed in FIG. 14, the median of the average pairwise resolution factors for a randomly chosen array generally fell between the average pairwise resolution factors for the original 9-member carbon black and PEDOT arrays. These results show that in most cases, the addition of a small number of carbon black detectors to the PEDOT array can increase its performance in discrimination of a broadly construed set of test solvents to approximately the same level as the array containing only carbon black detectors. The addition of carbon black detectors to an array of stable and well-behaved PEDOT PSS detectors also increases the performance significantly in the average pairwise resolution of nonpolar analytes from other nonpolar analytes.

Poly(3,4-ethylenedioxy)thiophene-based composite chemiresistor detector arrays are capable of classifying a test set of 16 analyte vapors from the relative differential resistance responses produced upon exposure to the analytes. The stability of the conductivity, low noise levels, and chemical diversity that can be achieved by using a multitude of insulating polymers in the composites make PEDOT-PSS an attractive material for use as the conducting component of composite chemiresistor arrays. The PEDOT-PSS composite detector array outperformed a carbon black composite array consisting of the same insulating polymers in the mean discrimination of pairs of polar compounds, whereas the carbon black array outperformed the PEDOT-PSS composite detector array in discriminating between pairs of nonpolar analytes. The increased sensitivity of PEDOT-containing films to polar analytes resulted predominantly from increased sensitvity of the electrically-conductive PEDOT regions to the sorption of analyte, as opposed to increased mass uptake of analyte by the composite film.

Although only a few embodiments have been described in detail above, those having ordinary skill in the art will certainly understand that many modifications are possible in the preferred embodiment without departing from the teachings thereof.

All such modifications are intended to be encompassed within the following claims.

What is claimed is:

1. A sensor, comprising:
    a sensor film separating and in direct contact with at least two conductive leads wherein the sensor film comprises regions of at least a first material having a positive temperature coefficient of resistance and a second non-conductive or insulating material compositionally different than the first material, wherein the sensor film provides an electrical path between the at least two conductive leads through and transverse to the regions of the first material and the regions of the second material, the first material being selected from the group consisting of a poly(3,4-ethylenedioxy) thiophene (polyEDOT), poly(3,4-ethylenedithiathiophene), and a poly(3,4-ethylenedioxy)thiophene-poly(styrene sulfonate) (PEDOT-PSS).

2. The sensor according to claim 1, wherein the first material is PEDOT-PSS.

3. The sensor according to claim 1, comprising regions of the first material, the second non-conductive or insulating material, and regions of a conductor, wherein the sensor provides an electrical path through the regions of the first material, the second material, and the conductor.

4. The sensor according to claim 3, wherein the conductor is selected from the group consisting of Ag, Au, Cu, Pt, carbon black, and AuCu.

5. The sensor of claim 1, wherein the second material is selected from the group consisting of poly(vinyl acetate), poly(epichlorohydrin), poly(ethylene oxide), poly(vinyl butyral), poly(n-butyl methacrylate), poly(caprolactone), poly(diallylphthalate), poly(2-hydroxyethylmethacrylate), vinyl chloride (91%)/vinyl acetate (6%)/vinyl alcohol (3%) copolymer, hydroxypropyl cellulose, poly(2-butadiene), cellulose propionate, poly(vinyl alcohol), poly(methyl vinyl ether) (50% solids in water), poly(styrene), and poly(4-vinyl phenol).

6. A sensor, comprising:
at least two conductive leads;
a sensor film separating and in direct contact with the at least two conductive leads wherein the sensor film comprises a plurality of alternating regions of differing compositions comprising differing conductivity transverse to the electrical path between the conductive leads, wherein at least one of the plurality of alternating regions comprising a first material selected from the group consisting of an emeraldine salt of polyaniline, a poly(3,4-ethylenedioxy)thiophene (polyEDOT), a poly (3,4-ethylenedioxy)thiophene-poly(styrene sulfonate) (PEDOT-PSS), and poly(3,4-ethylenedithiathiophene) and at least one other region of the plurality of alternating regions comprises a second material, wherein the second material is a non-conductive or insulating material.

7. The sensor of claim 6, wherein the first material is PEDOT-PSS.

8. A sensor, comprising:
at least two conductive leads;
a sensor film separating and in direct contact with the at least two conductive leads wherein the sensor film comprises a plurality of alternating regions of differing compositions comprising differing conductivity transverse to the electrical path between the conductive leads, wherein at least one of the plurality of alternating regions comprises poly(3,4-ethylenedioxy)thiophene-poly(styrene sulfonate) (PEDOT-PSS), and at least one other region of the plurality of alternating regions comprises a non-conductive or insulating material.

9. A sensor, comprising:
at least two conductive leads;
a sensor film separating and in direct contact with the at least two conductive leads wherein the sensor film comprises a plurality of alternating interpenetrating regions of differing compositions comprising differing conductivity between the conductive leads, wherein at least one of the plurality of alternating interpenetrating regions comprises a first material selected from the group consisting of an emeraldine salt of polyaniline, a poly(3,4-ethylenedioxy)thiophene (polyEDOT), a poly (3,4-ethylenedioxy)thiophene-poly(styrene sulfonate) (PEDOT-PSS), and poly(3,4-ethylenedithiathiophene) and at least one other region of the plurality of alternating interpenetrating regions comprises a second material, wherein the second material is a non-conductive or insulating material.

10. A sensor for detecting the presence of an analyte, the sensor comprising a chemically sensitive resistor electrically connected to an electrical measuring apparatus, the chemically sensitive resistor comprising:
at least two conductive leads; and
a sensor film separating and in direct contact with the at least two conductive leads wherein the sensor film comprises a region of at least a first material having a positive temperature coefficient of resistance and a second non-conductive or insulating material compositionally different than the first material, wherein the region provides an electrical path through and transverse to the regions of the first material and the regions of the second material, the first material being selected from the group consisting of an emeraldine salt of polyaniline, a poly(3,4-ethylenedioxy)thiophene (polyEDOT), poly(3,4-ethylenedithiathiophene) and a poly(3,4-ethylenedioxy)thiophene-poly(styrene sulfonate) (PEDOT-PSS),
whereby an electrical resistance is generated when the sensor is contacted with the analyte the electrical resistance thereby being used to detect the presence of an analyte.

11. The sensor of claim 10, wherein the first material is PEDOT-PSS.

* * * * *